(12) United States Patent
Soukharev et al.

(10) Patent No.: US 7,374,900 B2
(45) Date of Patent: May 20, 2008

(54) FLUORESCENT SUBSTRATES FOR DETECTING ORGANOPHOSPHATASE ENZYME ACTIVITY

(75) Inventors: Serguei Soukharev, Derwood, MD (US); David Hammond, Laytonsville, MD (US)

(73) Assignee: The American National Red Cross, Rockville, MD (US)

( * ) Notice: Subject to any disclaimer, the term of this patent is extended or adjusted under 35 U.S.C. 154(b) by 0 days.

(21) Appl. No.: 10/553,650

(22) PCT Filed: Mar. 16, 2004

(86) PCT No.: PCT/US2004/007897

§ 371 (c)(1), (2), (4) Date: Oct. 14, 2005

(87) PCT Pub. No.: WO2004/094658

PCT Pub. Date: Nov. 4, 2004

(65) Prior Publication Data

US 2007/0042370 A1 Feb. 22, 2007

Related U.S. Application Data

(60) Provisional application No. 60/487,935, filed on Jul. 18, 2003, provisional application No. 60/463,317, filed on Apr. 17, 2003.

(51) Int. Cl.
C12Q 1/42 (2006.01)
C07F 9/12 (2006.01)

(52) U.S. Cl. .......................... 435/21; 549/220

(58) Field of Classification Search ............... 549/471, 549/220; 435/21
See application file for complete search history.

(56) References Cited

U.S. PATENT DOCUMENTS

| | | | |
|---|---|---|---|
| 3,457,332 A | | 7/1969 | Scheinpflug et al. |
| 4,659,657 A | * | 4/1987 | Harnisch et al. .............. 435/21 |
| 5,011,964 A | | 4/1991 | Mynarcik et al. |
| 5,773,236 A | | 6/1998 | Diwu et al. |
| 5,830,666 A | | 11/1998 | Fujita et al. |
| 5,981,207 A | | 11/1999 | Yang et al. |
| 5,998,593 A | | 12/1999 | Huff et al. |

FOREIGN PATENT DOCUMENTS

| EP | 0 949 266 A | 10/1999 |
|---|---|---|
| GB | 972 981 A | 10/1964 |
| WO | WO 02/092803 A | 11/2002 |
| WO | WO 03/020734 A | 3/2003 |
| WO | WO 03/020984 A | 3/2003 |
| WO | WO 03/088990 A | 10/2003 |

OTHER PUBLICATIONS

Zhu et al, Organic Letters, vol. 5, No. 3, p. 1257-1260 (Apr. 17, 2003).*
Peter Kovacs et al., "Fluorimetric analysis of phospholipase activity in *Tetrahymena pyriformis* GL", Bioscience Reports, vol. 19, No. 2, Apr. 1999, pp. 81-87.
C. Schultz et al., "Acetoxymethyl Esters of Phosphates, Enhancement of the Permeability and Potency of Camp", Journal of Biological Chemistry, American Society of Biological Chemists, Baltimore MD, vol. 268, No. 9, Mar. 25, 1993, pp. 6316-6322.

(Continued)

*Primary Examiner*—Bernard Dentz
(74) *Attorney, Agent, or Firm*—Foley & Lardner LLP

(57) ABSTRACT

Disclosed are compounds of the formula (I): wherein $R^3$, $R^4$, $R^5$, $R^9$, and $R^{10}$ are selected from the group consisting of H and groups or atoms other than H, and $R^6$ and $R^8$ are halo or hydrogen; $X^1$, $X^2$, and $X^3$ are independently O or S; provided that $R^9$ and $R^{10}$ are not simultaneously H, when all of $X^1$, $X^2$, and $X^3$ are O; and of the formula (II) wherein $R^{11}$-$R^{14}$ are selected from the group consisting of H and groups or atoms other than H; $X^4$-$X^9$ are independently O or S; n and m are 0 or 1 but m and n cannot be 0 simultaneously; $R^{15}$-$R^{24}$ can be H or any substituent so long as the compound of formula II upon hydrolysis provides a fluorescent compound. These compounds are useful as substrates with high specificity for organophosphatase particularly human paraoxonase and bacterial organophosphorus hydrolase. Also disclosed is a method for detecting and/or measuring the paraoxonase activity in a fluid comprising contacting the fluid with a fluorescent substrate and measuring the fluorescence of the fluorescent product formed.

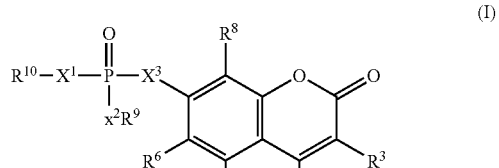

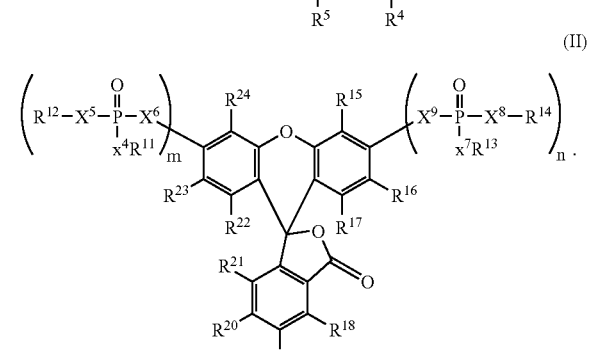

29 Claims, 8 Drawing Sheets

OTHER PUBLICATIONS

Kyle R. Gee et al., "Fluorogenic substrates based on fluorinated umbelliferones for continuous assays of phosphatases and beta-galactosidases", Analytical Biochemistry, vol. 273, No. 1, Aug. 15, 1999, pp. 41-48.

Z. Huang et al., "3,6-Fluorescein Diphosphaste: A Sensitive Fluorogenic and Chromogenic Substrate for Protein Tyrosine Phosphatates", Journal of Biomolecular Screening, Larchmont, NY, US, vol. 4, No. 6, Dec. 1999, pp. 327-334.

K R Gee, "Novel fluorogenic substrates for acid phosphatase", Bioorganic and Medicinal Chemistry Letters, Oxford GB, vol. 9, No. 10, May 17, 1999, pp. 1395-1396.

Tatiana O. Zaikova et al., "Synthesis of fluorogenic substrates for continuous assay of phosphatidylinositol-specific phospholipase C", Bioconjugate Chemistry, vol. 12, No. 2, Mar. 2001, pp. 307-313.

Q. Wang et al., "Novel caged fluorescein diphosphates as photoactivatable substrates for protein tyrosine phosphatases", Biochimica et Biophysica Acta, vol. 1601, No. 1, Nov. 19, 2002, pp. 19-28.

Lucio G. Costa, "Current issues in organophosphate toxicology", Clinica Chimica Acta 366 (2006) pp. 1-13.

* cited by examiner

FLUORESCENT SUBSTRATES FOR DETECTING ORGANOPHOSPHATASE ENZYME ACTIVITY

CROSS-REFERENCE TO RELATED APPLICATIONS

This application claims the benefit of U.S. provisional patent application Nos. 60/463,317, filed Apr. 17, 2003 and 60/487,935, filed Jul. 18, 2003, the disclosures of which are incorporated by reference.

FIELD OF THEE INVENTION

This invention relates to certain fluorescent substrates and a method for detecting organophosphatase activity in general, and paraoxonase activity specifically and in particular in biological fluids such as blood and serum, through the use of such fluorescent substrates.

BACKGROUND OF THE INVENTION

Enzymatic degradation of organophosphates (OPs) is performed by specialized enzymes including bacterial organophosphorus hydrolase (OPH) and mammalian paraoxonase. Paraoxonase also referred to as, arylesterase (EC 3.1.1.2) is a 43 kDa molecular weight calcium dependent ester hydrolase that catalyses the hydrolysis of a broad range of esters such as OPs, and unsaturated aliphatic and aromatic carboxylic esters. Its name derives from the ability of this protein to hydrolyze paraoxon, the toxic metabolite of the insecticide parathion. In addition to paraoxon, paraoxonase is able to detoxify a number of other insecticides, e.g. diazonin, as well as the potent nerve gases sarin and soman that target acetylcholinesterase (AChE). The paraoxonase gene (PON) family consists of at least three members: PON1, PON2 and PON3, which are located on the human 7q21.3-22.1 chromosome. No significant endogenous expression of PON2 and PON3 genes has been detected. Most PON1 expression takes place in the human liver; from there the protein is secreted into blood where it circulates associated with high density lipoprotein (HDL) particles. Paraoxonase has the unusual property that the mature protein retains its hydrophobic N-terminal signal peptide, which is used as an anchor for association with HDL. The enzyme has three potential N-linked sites and carbohydrate accounts for approximately 16% of its molecular mass.

There is a significant variation in paraoxonase activity in the human population, which is a result of polymorphism in the PON1 promoter that leads to different levels of expression, as well as polymorphism in gene sequence that leads to allele forms of protein with different specific activity. Both types of polymorphisms are quite common among the human population generating a range of paraoxonase serum activity in the population. The apparent molecular mass of serum paraoxonase varies as the result of heterogeneous glycosylation.

Neither the function nor natural substrate(s) for paraoxonase have yet been identified. One possible substrate is oxidized low density lipoprotein (LDL) [1-3]. Paraoxonase has been shown both to prevent formation of oxidized LDL and to hydrolyze LDL-derived oxidized phospholipids. Since accumulation of oxidized LDL is one of the key factors in development of atherosclerosis, paraoxonase activity may correlate with development of this disease. For example, Shih et al demonstrated that PON1 −/− mice were extremely sensitive to diet-induced atherosclerosis in comparison with wild type mice. Since there is a significant variation in paraoxonase activity among the population, evaluation of paraoxonase levels of individuals may have a significant diagnostic value, predicting the chances, development and prognosis of atherosclerosis.

Another possible natural substrate is lipopolysaccharide (LPS) or mediators of septic shock. It has been shown that high density lipoprotein (HDL) can inactivate LPS [4]. Moreover, intraperitoneal injection of mice before and up to 2 hours after LPS administration afforded protection against septic shock [5]. In addition, PON-1 knockout mice are extremely sensitive to LPS [6].

Paraoxonase is able to hydrolyze a number of OP toxins in vitro, and the ability of paraoxonase to protect animals in acute OP poisoning has been extensively studied. Injection of purified paraoxonase protected animals against OP toxicity [7, 8]. Further proof of the ability of paraoxonase to protect animals has been obtained from studies on PON1 "knock-out" mice. Destruction of the PON1 gene by knock-out technology creates mice that lack paraoxonase. Compared to wild type littermates, PON1 deficient mice were extremely sensitive to the toxic effects of chlorpyrifos, an OP. Thus, monitoring of paraoxonase activity may help to evaluate a person's ability to withstand OP poisoning associated with deployment of chemical weapons.

Consequently, monitoring blood levels of paraoxonase may be used to identify a predisposition to atherosclerosis, sepsis and OP poisoning. However, the absence of a robust test for detection of paraoxonase levels in blood has significantly delayed progress in studying the diagnostic value of paraoxonase. There are two major options for detection of this enzyme activity. The first is a change in optical density and the second the generation of a fluorescent product.

Currently, the most common substrates for paraoxonase used in research are paraoxon and phenylacetate. Paraoxonase catalyzed hydrolyses of paraoxon leads to release of nitrophenol, which can be detected by monitoring adsorption at 405 nm. This reaction is used to measure paraoxonase activity in fundamental and clinical research. The main disadvantages of this substrate are the low Vmax of hydrolysis, which results in relatively low sensitivity and, due to its toxicity, paraoxon requires special handling conditions. The arylesterase activity of paraoxonase is usually measured through hydrolysis of phenylacetate. This reaction has a much higher Vmax, than the Vmax of paraoxon hydrolysis; however, phenylacetate is also hydrolyzed by a number of other esterases in cell extracts and serum samples, which significantly decreases the specificity of detection. In addition, the detection of phenylacetate hydrolysis is based on monitoring adsorption at 270 nm making paraoxonase detection difficult, or impossible, in protein rich solutions or in extracts containing detergents like Triton X-100.

The OPH gene was originally found in two soil microorganisms, *Pseudomonas diminuta* and *Flavobacterium* sp. It has been suggested that this enzyme evolved recently in these bacteria in response to industrial soil contamination with organophosphate compounds. Like paraoxonase, OPH catalyzes a broad range of organophosphate esters including sarin and VX. Due to this activity these organisms may have additional utility in decontamination of OPs in the environment. In this context a sensitive and robust assay would be necessary to confirm expression of OPH in the presence of a large excess of phosphatase activity. Thus, it is essential that the substrate has very little or no affinity for phosphatases.

The foregoing shows that there exists a need for detecting organophosphatase activity including paraoxonase with high specificity and sensitivity. There exists a need for substrates with high specificity for OPH and paraoxonase. The advantages of the present invention as well as inventive features will be apparent from the detailed description of the embodiments of the invention provided herein.

BRIEF SUMMARY OF THE INVENTION

The foregoing needs have been fulfilled to a great extent. The present invention provides highly sensitive and specific fluorescent substrates. In accordance with an embodiment, the present invention provides compounds of the formula (I):

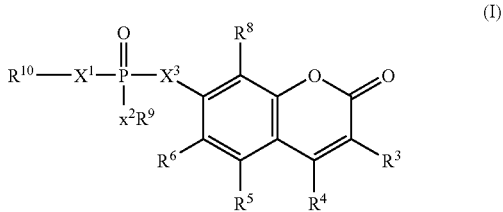

wherein $R^3$, $R^4$, $R^5$, $R^9$, and $R^{10}$ are selected from the group consisting of H and groups or atoms other than H, and $R^6$ and $R^8$ are halo or hydrogen; $X^1$, $X^2$, and $X^3$ are independently O or S; provided that $R^9$ and $R^{10}$ are not simultaneously H, when all of $X^1$, $X^2$, and $X^3$ are O.

In accordance with another embodiment, the present invention provide compound of the formula II:

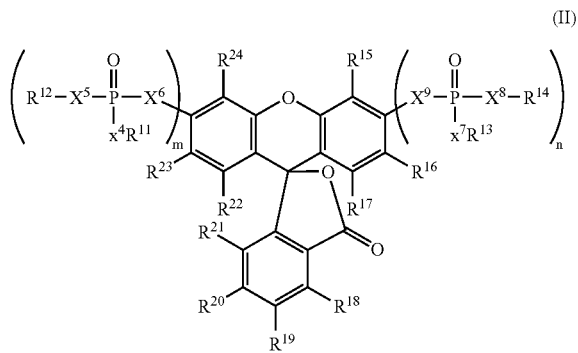

wherein $R^{11}$-$R^{14}$ are selected from the group consisting of H and groups or atoms other than H; $X^4$-$X^9$ are independently O or S. n and m are 0 or 1 but m and n cannot be 0 simultaneously. $R^{15}$-$R^{24}$ can be H or any substituent so long as the compound of formula II upon hydrolysis provides a fluorescent compound.

The present invention also provides a method for detecting and/or measuring the organophosphatases and particularly paraoxonase activity in a fluid comprising contacting the fluid with a fluorescent substrate and measuring the fluorescence of the fluorescent product formed.

The fluorescent substrates of this invention are specific for organophosphatases including paraoxonase and, when hydrolyzed, release highly fluorescent products which can be measured at, for example, an emission wavelength of 460 nm following excitation at a wavelength of 355 nm for structures based on the coumarin structure and emission of 520 nm following excitation at 488 nm for fluorescein-based structures. In comparison with the other substrates used for the detection of paraoxonase, these have significantly higher sensitivity and specificity. The substrates of the present invention facilitate large through put methods for the detection and quantitation of this enzyme's activity. Such methods may be used for detection of paraoxonase as a diagnostic marker for prediction of atherosclerosis development, sepsis and sensitivity to OPs.

The substrates are useful for detecting and quantifying paraoxonase activity in samples of biological fluids such as blood. Measurement of blood paraoxonase activity may be useful as an indicator of cardiovascular disease and sensitivity to OP poisoning. Also provided is a method for detecting the activity of paraoxonase in an environmental sample. Such samples may include those which have been treated with paraoxonase to decontaminate OPs. Also provided is a method for studying the basic properties of paraoxonase by using these substrates as research reagents. Also provided is a method of assaying for the presence of OPs through the specific inhibition of substrate induced fluorescence. The substrates of the present invention have one or more than one advantage; e.g., high specificity for paraoxonase; high sensitivity fluorescent detection and a significant Vmax of reaction makes it at least 10-20 times more sensitive than any other known substrate for paraoxonase detection. Consequently, the substrates may have a significant practical use in different areas of medicine and detection of nerve gas poisons.

The substrates are useful for detecting and quantifying OPH activity in environmental samples such as soil extracts or swabs. Such samples may include those which have been treated with OPH to decontaminate OPs. Also provided is a method for studying the basic properties of OPH by using these substrates as research reagents. Also provided is a method of assaying for the presence of OPs through the specific inhibition of substrate induced fluorescence. The substrates of the present invention have one or more than one advantage; e.g., high specificity for OPH; high sensitivity fluorescent detection and a significant Vmax of reaction makes it at least 10-20 times more sensitive than any other known substrate for OPH detection. Consequently, the substrates may have a significant practical use in different areas of medicine and detection of nerve gas poisons.

The proposed substrates can be used for broad screening of paraoxonase activity in human blood. Paraoxonase levels in the blood correlates with resistance to organophosphate poisoning, development of atherosclerosis, ability to detoxify LPS and general liver malfunctions. The present invention provides an assay kit for paraoxonase detection and quantitation. Such a kit may be used for detection of paraoxonase as a diagnostic marker for prediction of atherosclerosis development. The diagnostic prognosis of paraoxonase detection is comparable to, or better than, such blood markers as blood cholesterol level. Such a kit may also be used for detection of paraoxonase as a diagnostic marker for prediction of sepsis development. Another potential use of a kit for detection of paraoxonase is predicting the resistance to OP challenges which can have a significant value in a war against chemical terrorism or during combat where chemical weapons are utilized. It is also envisaged that the kit may be used to confirm that protective levels of paraoxonase have been achieved in war fighters following administration of prophylactic levels of recombinant paraoxonase. Moreover, a rapid and sensitive method for detection of organophosphatase activity may be useful for the detection of alternative substrates, e.g., nerve poisons, OP toxins and insecticides, present in environment samples.

Such alternative substrates for organophosphatase may be identified by their ability to compete for binding and hydrolysis of the substrates of the present invention.

The present invention further provides a method for selectively detecting organophosphatase in a sample suspected to contain organophosphatase and a phosphatase comprising contacting the sample with a substrate of the invention, measuring the fluorescence of a fluorescent product formed during the contacting; and correlating the measured fluorescence with the activity of the organophosphatase enzyme. The spectrum of structures provides a method to discover different organophosphatases with different spectra of substrate specificities.

The present invention further provides a method for detecting and/or measuring the activity of organophosphatase enzyme immobilized on a support comprising contacting the support with a substrate of the invention, measuring the fluorescence of a fluorescent product formed during the contacting; and correlating the measured fluorescence with the activity of the organophosphatase enzyme.

While the invention has been described and disclosed below in connection with certain embodiments and procedures, it is not intended to limit the invention to those specific embodiments. Rather it is intended to cover all such alternative embodiments and modifications as fall within the spirit and scope of the invention.

DETAILED DESCRIPTION OF EMBODIMENTS

Figure 1:
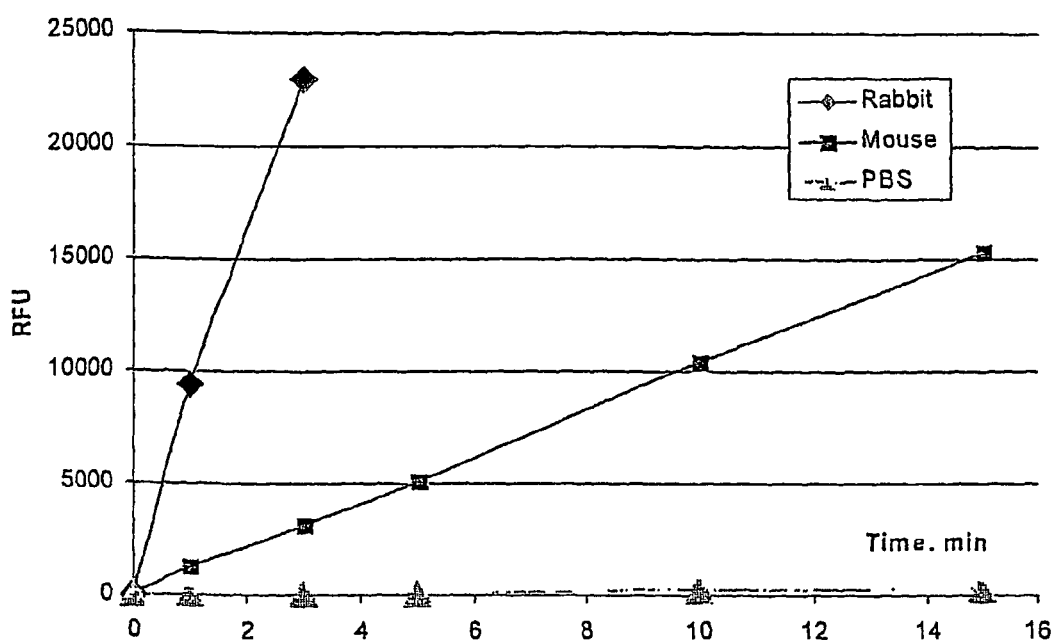
FIG. 1 depicts the detection of paraoxonase activity in serum samples using 7-[diethyl-phosphor]-6,8-difluoro-4-methylumbelliferyl (DEPFMU) as a substrate. In this assay 10 µl of rabbit and, separately 10 µl of mouse serum both previously diluted 10 fold with assay buffer, 20 mM Tris.HCl, pH 8.0, 150 mM NaCl and 2 mM $CaCl_2$, were incubated with 100 µl of assay buffer containing 100 µM of DEPFMU. The rates of change of fluorescence at 37° C. were monitored at 355/460.

The present invention provides a compound of the formula I:

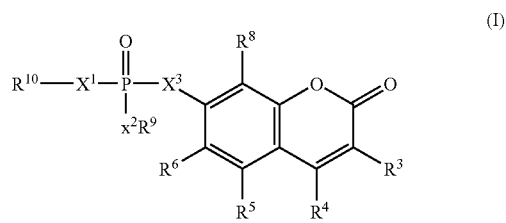

wherein $R^3$, $R^4$, $R^5$, $R^9$, and $R^{10}$ are selected from the group consisting of H and groups or atoms other than H, and $R^6$ and $R^8$ are halo or hydrogen; $X^1$, $X^2$, and $X^3$ are independently O or S; provided that $R^9$ and $R^{10}$ are not simultaneously H, when all of $X^1$, $X^2$, and $X^3$ are O.

In accordance with an embodiment of the invention in formula I, $R^3$, $R^4$, and $R^5$ are selected from the group consisting of H, hydroxyl, cyano, nitro, halo, amino, amido, azido, acetal, ketal, imido, sulfo, sulfonyl, sulfinyl, sulfomethyl, a salt of sulfomethyl, thiocyanato, aldehydo, keto, carbamoyl, urethane, ureido, guanidino, $C_1$-$C_6$ alkylamino, $C_1$-$C_6$ acylamino, $C_1$-$C_6$ alkylamido, $C_1$-$C_6$ alkyl, $C_1$-$C_6$ alkoxy, $C_1$-$C_6$ alkylthio, $C_5$-$C_8$ cycloalkyl, $C_1$-$C_6$ haloalkyl, $C_1$-$C_6$ perfluoroalkyl, formyl, carboxamide of the formula —(C═O)NR$^1$R$^2$ where $R^1$ and $R^2$ are independently H, alkyl having 1-6 carbon atoms, an aryl, or $R^1$ and $R^2$ taken together form a saturated 5- or 6-membered ring having the formula —(CH$_2$)$_2$-M-(CH$_2$)$_2$— where the ring moiety M is a single bond, an oxygen atom, a methylene group, or the secondary amine —NR$^7$— where $R^7$ is H or alkyl having 1-6 carbon atoms, $C_5$-$C_8$ halocycloalkyl, $C_1$-$C_6$ hydroxyalkyl, $C_5$-$C_8$ hydroxycycloalkyl, $C_1$-$C_6$ alkoxy $C_1$-$C_6$ alkyl, $C_2$-$C_6$ alkoxycarbonyl, $C_2$-$C_6$ alkoxycarbonyl $C_1$-$C_6$ alkyl, carboxy $C_1$-$C_6$ alkyl, carboxy $C_1$-$C_6$ alkoxy, dicarboxy $C_1$-$C_6$ alkyl, dicarboxy $C_1$-$C_6$ alkoxy, $C_2$-$C_6$ cyanoalkyl, phosphono $C_1$-$C_6$ alkyl, phosphoryl $C_1$-$C_6$ alkyl, mono-, di-, and trisaccharides, nucleic acids, oligonucleotides, amino acids, peptides, and proteins, and $C_2$-$C_6$ alkenyl, $C_2$-$C_6$ alkynyl, aryl, arylcarbonyl, and heteroaryl, which may be optionally substituted with a substituent selected from the group consisting of hydroxyl, cyano, nitro, halo, amino, amido, azido, acetal, ketal, imido, sulfo, sulfonyl, sulfinyl, thiocyanato, aldehydo, keto, carbamoyl, urethane, ureido, and guanidino; $R^9$ and $R^{10}$ are selected from the group consisting of H, $C_1$-$C_6$ alkyl, $C_5$-$C_8$ cycloalkyl, $C_1$-$C_6$ haloalkyl, $C_1$-$C_6$ perfluoroalkyl, $C_2$-$C_6$ alkenyl, $C_2$-$C_6$ alkynyl, aryl, arylcarbonyl, heteroaryl, $C_1$-$C_6$ aminoalkyl, $C_5$-$C_8$ cycloalkyl, $C_1$-$C_6$ haloalkyl, $C_5$-$C_8$ halocycloalkyl, $C_1$-$C_6$ hydroxyalkyl, $C_5$-$C_8$ hydroxycycloalkyl, $C_1$-$C_6$ alkoxy $C_1$-$C_6$ alkyl, $C_2$-$C_6$ alkoxycarbonyl, $C_2$-$C_6$ alkoxycarbonyl $C_1$-$C_6$ alkyl, carboxy $C_1$-$C_6$ alkyl, carboxy $C_1$-$C_6$ alkoxy, dicarboxy $C_1$-$C_6$ alkyl, dicarboxy $C_1$-$C_6$ alkoxy, $C_2$-$C_6$ cyanoalkyl, phosphono $C_1$-$C_6$ alkyl, phosphoryl $C_1$-$C_6$ alkyl, mono-, di-, and trisaccharides, nucleic acids, oligonucleotides, amino acids, peptides, and proteins, and $C_2$-$C_6$ alkenyl, $C_2$-$C_6$ alkynyl, aryl, and heteroaryl, which may be optionally substituted with a substituent selected from the group consisting of hydroxyl, cyano, nitro, halo, amino, amido, azido, acetal, ketal, imido, sulfo, sulfonyl, sulfinyl, thiocyanato, aldehydo, keto, carbamoyl, urethane, ureido, and guanidino; and $R^6$ and $R^8$ are halo, particularly fluoro.

In accordance with an embodiment of the invention in formula I, $R^4$ is selected from the group consisting of H, hydroxyl, cyano, nitro, halo, amino, amido, azido, acetal, ketal, imido, sulfo, sulfonyl, sulfinyl, sulfomethyl, salt of sulfomethyl, thiocyanato, aldehydo, keto, carbamoyl, urethane, ureido, guanidino, $C_1$-$C_6$ alkylamino, $C_1$-$C_6$ acylamino, $C_1$-$C_6$ alkylamido, $C_1$-$C_6$ alkyl, $C_1$-$C_6$ alkoxy, $C_1$-$C_6$ perfluoroalkyl, halomethyl, $C_1$-$C_6$ alkylthio, $C_5$-$C_8$ cycloalkyl, $C_1$-$C_6$ haloalkyl, $C_5$-$C_8$ halocycloalkyl, $C_1$-$C_6$ hydroxyalkyl, $C_5$-$C_8$ hydroxycycloalkyl, $C_1$-$C_6$ alkoxy $C_1$-$C_6$ alkyl, $C_2$-$C_6$ alkoxycarbonyl, $C_2$-$C_6$ alkoxycarbonyl $C_1$-$C_6$ alkyl, carboxy $C_1$-$C_6$ alkyl, carboxy $C_1$-$C_6$ alkoxy, dicarboxy $C_1$-$C_6$ alkyl, dicarboxy $C_1$-$C_6$ alkoxy, $C_2$-$C_6$ cyanoalkyl, phosphono $C_1$-$C_6$ alkyl, phosphoryl $C_1$-$C_6$ alkyl, mono-, di-, and trisaccharides, nucleic acids, oligonucleotides, amino acids, peptides, and proteins, and $C_2$-$C_6$ alkenyl, $C_2$-$C_6$ alkynyl, aryl, arylcarbonyl, and heteroaryl, which may be optionally substituted with a substituent selected from the group consisting of hydroxyl, cyano, nitro, halo, amino, amido, azido, acetal, ketal, imido, sulfo, sulfonyl, sulfinyl, thiocyanato, aldehydo, keto, carbamoyl, urethane, ureido, and guanidino. In a preferred embodiment, $R^4$ is selected from the group consisting of H, cyano, sulfomethyl, salt of sulfomethyl, aryl, $C_1$-$C_6$ alkyl, $C_1$-$C_6$ alkoxy, and $C_1$-$C_6$ perfluoroalkyl, more preferably $C_1$-$C_6$ alkyl, for example, methyl.

In accordance with an embodiment of the invention in formula I, $R^9$ and $R^{10}$ are selected from the group consisting of H, $C_1$-$C_6$ alkyl, $C_5$-$C_8$ cycloalkyl, $C_1$-$C_6$ haloalkyl, $C_1$-$C_6$ perfluoroalkyl, $C_2$-$C_6$ alkenyl, and $C_2$-$C_6$ alkynyl, and aryl, arylcarbonyl, and heteroaryl, which may be optionally substituted with a substituent selected from the group consisting of hydroxyl, cyano, nitro, halo, amino, amido, azido, acetal, ketal, imido, sulfo, sulfonyl, sulfinyl, thiocyanato, aldehydo, keto, carbamoyl, urethane, ureido, and guanidino; and $X^1$, $X^2$, and $X^3$ are O or S, preferably O.

In a preferred embodiment of formula I, $R^9$ and $R^{10}$ are selected from the group consisting of H, $C_1$-$C_6$ alkyl, $C_2$-$C_6$ alkenyl, $C_2$-$C_6$ alkynyl, aryl, and heteroaryl, more preferably from the group consisting of H, $C_1$-$C_6$ alkyl, $C_2$-$C_6$ alkenyl, and $C_2$-$C_6$ alkynyl. In a further preferred embodiment, $R^9$ and $R^{10}$ are selected from the group consisting of $C_1$-$C_6$ alkyl, for example, $R^9$ and $R^{10}$ are ethyl.

In accordance with another embodiment of formula I, $R^3$ is selected from the group consisting of H, cyano, $C_1$-$C_6$ alkyl, $C_1$-$C_6$ perfluoroalkyl, $C_2$-$C_6$ alkenyl, $C_2$-$C_6$ alkynyl, aryl, and heteroaryl, formyl, carboxamide of the formula —C(=O)$NR^1R^2$ where $R^1$ and $R^2$ are independently H, alkyl having 1-6 carbon atoms, an aryl, or $R^1$ and $R^2$ taken together form a saturated 5- or 6-membered ring having the formula —(CH$_2$)$_2$-M-(CH$_2$)$_2$—where the ring moiety M is a single bond, an oxygen atom, a methylene group, or the secondary amine —NR$^7$— where $R^7$ is H or alkyl having 1-6 carbon atoms.

In accordance with an embodiment of formula I, $R^5$ is H or $C_1$-$C_6$ alkoxy, preferably H. In accordance with a preferred embodiment of formula I, $R^6$ and $R^8$ are fluoro. Examples of preferred compounds include those wherein $X^1$, $X^2$, and $X^3$ are O or S, more preferably O, $R^9$ and $R^{10}$ are ethyl, $R^4$ is methyl, $R^6$ and $R^8$ are fluoro, and $R^3$ and $R^5$ are H. Specific examples of the compound of formula I are those wherein $R^9$ and $R^{10}$ are ethyl, $R^4$ is methyl, $R^1$ and $R^8$ are fluoro, and $X^1$, $X^2$, and $X^3$ are O; and those wherein $X^1$ and $X^2$ are O, $X^3$ is S, $R^6$ and $R^8$ are H; $R^9$ and $R^{10}$ are ethyl, and $R^4$ is methyl.

The compounds of the present invention can be prepared by any suitable method, for example, by following methods generally known in the art; see, e.g., U.S. Pat. Nos. 4,659, 657; 5,423,059; 5,830,912; and 6,416,970; and U.S. patent application publication No. US 2003/0032080 A1; the disclosures of which are incorporated by reference. For example, the appropriate 7-hydroxycoumarin can be reacted with a suitable phosphate (or thiophosphate) ester compound to obtain the desired ester or thioester. For the preparation of dye conjugates, see G. T. Hermanson, *Bioconjugate Techniques* (Academic Press 1996).

The present invention provides a compound of the formula II:

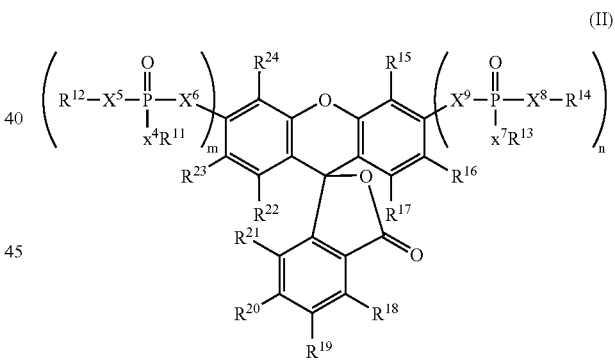

wherein $R^{11}$—$R^{14}$ are selected from the group consisting of H and groups or atoms other than H; $X^4$-$X^9$ are independently O or S. m and n are 0 or 1 but m and n cannot be 0 simultaneously. $R^{15}$-$R^{24}$ can be H or any substituent so long as the compound of formula II upon hydrolysis, e.g., of the P—$X^6$ and/or P—$X^9$ bonds, provides a fluorescent compound. When m or n is 0, the substituent at that position is H.

In an embodiment of the formula II, $R^{11}$-$R^{14}$ are independently selected from the group consisting of H, $C_1$-$C_6$ alkyl, $C_5$-$C_8$ cycloalkyl, $C_1$-$C_6$ haloalkyl, $C_1$-$C_6$ perfluoroalkyl, $C_2$-$C_6$ alkenyl, and $C_2$-$C_6$ alkynyl, and aryl, arylcarbonyl, and heteroaryl, which may be optionally substituted with a substituent selected from the group consisting of hydroxyl, cyano, nitro halo, amino, amido, azido, acetal, ketal, imido, sulfo, sulfonyl, sulfinyl, thiocyanato, aldehydo, keto, carbamoyl, urethane, ureido, and guanidino; and $X^4$-$X^9$ are independently O or S, preferably O. In a preferred embodiment, m and n are 1.

In accordance with an embodiment of the invention in formula II, $R^{15}$-$R^{24}$ are independently selected from the group consisting of H, hydroxyl, cyano, nitro, halo, amino, amido, azido, acetal, ketal, imido, sulfo, sulfonyl, sulfinyl, sulfomethyl, a salt of sulfomethyl, thiocyanato, aldehydo, keto, carbamoyl, urethane, ureido, guanidino, $C_1$-$C_6$ alkylamino, $C_1$-$C_6$ acylamino, $C_1$-$C_6$ alkylamido, $C_1$-$C_6$ alkyl, $C_1$-$C_6$ alkoxy, $C_1$-$C_6$ alkylthio, $C_5$-$C_8$ cycloalkyl, $C_1$-$C_6$ haloalkyl, $C_1$-$C_6$ perfluoroalkyl, formyl, carboxamide of the formula —(C=O)$NR^1R^2$ where $R^1$ and $R^2$ are independently H, alkyl having 1-6 carbon atoms, an aryl, or $R^1$ and $R^2$ taken together form a saturated 5- or 6-membered ring having the formula —$(CH_2)_2$-M-$(CH_2)_2$— where the ring moiety M is a single bond, an oxygen atom, a methylene group, or the secondary amine —$NR^7$— where $R^7$ is H or alkyl having 1-6 carbon atoms, $C_5$-$C_8$ halocycloalkyl, $C_1$-$C_6$ hydroxyalkyl, $C_5$-$C_8$ hydroxycycloalkyl, $C_1$-$C_6$ alkoxy $C_1$-$C_6$ alkyl, $C_2$-$C_6$ alkoxycarbonyl, $C_2$-$C_6$ alkoxycarbonyl $C_1$-$C_6$ alkyl, carboxy $C_1$-$C_6$ alkyl, carboxy $C_1$-$C_6$ alkoxy, dicarboxy $C_1$-$C_6$ alkyl, dicarboxy $C_1$-$C_6$ alkoxy, $C_2$-$C_6$ cyanoalkyl, phosphono $C_1$-$C_6$ alkyl, phosphoryl $C_1$-$C_6$ alkyl, mono-, di-, and trisaccharides, nucleic acids, oligonucleotides, amino acids, peptides, and proteins, and $C_2$-$C_6$ alkenyl, $C_2$-$C_6$ alkynyl, aryl, arylcarbonyl, and heteroaryl, which may be optionally substituted with a substituent selected from the group consisting of hydroxyl, cyano, nitro, halo, amino, amido, azido, acetal, ketal, imido, sulfo, sulfonyl, sulfinyl, thiocyanato, aldehydo, keto, carbamoyl, urethane, ureido, and guanidino.

In a preferred embodiment of the compound of formula II, $R^{11}$-$R^{14}$ are independently selected from the group consisting of H, $C_1$-$C_6$ alkyl, $C_2$-$C_6$ alkenyl, $C_2$-$C_6$ alkynyl, aryl, and heteroaryl, more preferably from the group consisting of H, $C_1$-$C_6$ alkyl, $C_2$-$C_6$ alkenyl, and $C_2$-$C_6$ alkynyl. In a further preferred embodiment, $R^{11}$-$R^{14}$ are independently selected from the group consisting of $C_1$-$C_6$ alkyl, for example, $R^{11}$-$R^{14}$ are ethyl, and m and n are 1. Specific examples are a compound wherein $X^4$-$X^9$ are O, $R^{15}$—$R^{24}$ are H, $R^{11}$-$R^{14}$ are ethyl; and m and n are 1 and a compound wherein $X^4$, $X^5$, $X^7$, and $X^8$ are O; $X^6$ and $X^9$ are S; $R^{15}$-$R^{24}$ are H; $R^{11}$—$R^{14}$ are ethyl; and m and n are 1.

In the compounds of formula I and II, aryl is a 1-3 aromatic ring containing group, preferably phenyl; heteroaryl is a 5- or 6-membered aromatic heterocycle that is optionally fused to an additional 6-membered aromatic ring or to one or more heteroaromatic ring containing 1-3 heteroatoms selected from the group consisting of O, N, and S. Examples of heteroaryl include pyrrole, thiophene, furan, oxazole, isooxazole, or imidazole, benzoxazole, benzothiazole, benzimidazole, benzofuran, and indole.

The compounds of formula II can be prepared by any suitable method. For example, fluorescein diphosphate tetraethyl ester can be prepared as shown in Example 10.

In an embodiment, the compounds of the present invention can be linked or conjugated to other molecules, groups, or substance, e.g., a dye, a reactive group, an antibody, or a solid support.

"Assay Buffer" is the buffer used in the detection of paraoxonase activity and is composed of 20 mM Tris.HCl, 150 mM NaCl and 2 mM $CaCl_2$ at pH 8.0 at 25° C.

"Biological fluid" is a sample of a fluid originating from a biological source. Examples of biological fluids include, but are not limited to blood, blood-derived compositions, serum, cerebrospinal fluid, urine, saliva, milk, ductal fluid, tears, semen, cell or tissue extracts, culture medium from the expression of paraoxonase or mutations of paraoxonase, samples arising from the fractionation of paraoxonase or HDL from biological samples.

"DEPFMU" is the abbreviation for 7-diethyl-phospho-6, 8-difluoro-4-methylumbelliferyl, a chemical compound that is one of the newly invented fluorogenic substrates for detection of paraoxonase activity "Environmental sample" is a sample obtained from the environment for purposes of detection of paraoxonase or OPs. It may be soil, water, air or any other material obtained natural environment.

"FDPTEE" is the abbreviation for fluorescein diphosphate tetraethyl ester.

"OP" is the abbreviation for organophosphate, which includes a variety of organic compounds that contain phosphorus and often have intense neurotoxic activities. This includes such compounds as sarin and soman, which were originally developed as nerve gases, as well as others widely used as insecticides and fire retardants.

OPH refers to the protein encoded by organophosphorus hydrolase which is expressed by two soil dwelling bacteria, Pseudomonas diminuta and Flavobacterium sp. It hydrolyses a number of organic esters including paraoxon.

"Paraoxonase" refers to the protein encoded by PON1 gene. Paraoxonase is a serum protein that possesses enzymatic activity. It hydrolyzes a number of organic and phospho-organic esters including paraoxon. The physiological function of paraoxonase is not known with certainty.

"PON1" refers to the gene encoding the protein known as paraoxonase, or arylesterase (EC 3.1.1.2). Paraoxonase is present in normal human plasma and the cDNA, and genes encoding the human protein have been sequenced and characterized.

"Substrate for organophosphatase" refers to one of a number of chemical compounds that are hydrolyzed by OPH and/or paraoxonase. These include DEPFMU, phenyl acetate, oxidized lipids and paraoxon.

"355/460" refers to an excitation wavelength of 355 nm and an emission wavelength of 460 nm.

The present invention further provides a method for detecting and/or measuring the activity of organosphosphatase in a fluid comprising contacting the fluid with a compound of formula I, wherein $R^3$-$R^6$ and $R^8$-$R^{10}$ can be any atom or group and $X^1$, $X^2$, and $X^3$ are independently O or S; or of the formula II, wherein $R^{11}$-$R^{14}$ are selected from the group consisting of H and groups or atoms other than H; $X^4$-$X^9$ are independently O or S. n and m are 0 or 1 but m and n cannot be 0 simultaneously. $R^{15}$-$R^{24}$ can be H or any substituent so long as the compound of formula II upon hydrolysis provides a fluorescent compound; measuring the fluorescence of a fluorescent product formed during the contacting; and correlating the measured fluorescence with the activity of the paraoxonase enzyme. Any of the compounds described above in paragraphs [0029]-[0036] and [0038]-[0042]may be employed in the method of the present invention.

In an embodiment of the method of detecting and/or measuring the activity of paraoxonase, the compound of formula I can be one wherein $R^3$, $R^4$, $R^5$, $R^9$, and $R^{10}$ are selected from the group consisting of H and groups or atoms other than H, and $R^6$ and $R^8$ are halo. In an embodiment of the method of detecting and/or measuring the activity of paraoxonase, the compound of formula II can be one wherein $X^4$-$X^9$ are O, m and n are 1, $R^{11}$-$R^{24}$ are H.

In accordance with an embodiment, the compounds described above can be used for detection of organophosphatase activity and specifically paraoxonase activity in a biological fluid. Examples of biological fluids include, but are not limited to, blood, blood-derived compositions or serum, cerebrospinal fluid, urine, saliva, milk, ductal fluid, tears, semen, brain, artery, vein and gland extracts. Other fluids may contain culture medium from the expression of paraoxonase or mutations of paraoxonase. Still further fluids may be taken from methods and processes resulting in the fractionation of paraoxonase or HDL from biological samples. In an embodiment, the fluid is an environmental fluid, for example, an extract of soil, water, or swab.

In accordance with an embodiment, the compounds described above can be used for detection of organophosphatase activity and specifically OPH activity in a biological fluid or environmental extract. Examples of biological fluids include, but are not limited to, blood, blood-derived compositions or serum, cerebrospinal fluid, urine, saliva, milk, ductal fluid, tears, semen, brain, artery, vein and gland extracts. Other fluids may contain culture medium from the expression of OPH or mutations of OPH. Still further fluids may be taken from methods and processes resulting in the fractionation of OPH from biological samples. In an embodiment, the fluid is an environmental fluid, for example, an extract of soil, water, or swab.

In a further embodiment, the present invention provides a method for predicting the existence of cardiovascular diseases. The present invention further provides a method for predicting a person's sensitivity to OPs. The activity of paraoxonase as measured using the compounds of the present invention can be used as a predictor of cardiovascular disease and sensitivity to OPs.

In a further embodiment, the present invention provides a method for predicting the potential for septic shock. The present invention further provides a method for predicting a person's sensitivity to LPS. The activity of paraoxonase as measured using the compounds of the present invention can be used as a predictor of sensitivity to LPS.

In another embodiment, the present invention provides a method for evaluating and/or predicting the functional activity of preparations of HDL. The paraoxonase activity measured by the fluorescence in accordance with the present invention may be used for evaluation/prediction of functional activity of preparations of high density lipoproteins.

In a further embodiment, detection of fluorescence is achieved using an excitation wavelength and an emission wavelength. In a further embodiment, OPH and paraoxonase activity can be monitored using a fluorimeter with an excitation wavelength at 355 nm and an emission wavelength at 460 nm. Other assay formats include analysis of OPH activity in gels after protein separation by electrophoresis or analysis of paraoxonase expression/secretion in live or dead cells embedded in low melting point agarose, immunoblotting, western blot analysis, and fluorescent detection in situ with detection by microscopy, visual inspection, via film. Alternatively OPH or paraoxonase may be immobilized on supports such as membranes, resins or dipsticks.

In a further embodiment, organophosphatase activity may be detected on the surface of cells expressing paraoxonase activity using a cell sorter (e.g., fluorescence assisted cell sorter or FACS).

In a further embodiment the compounds of the present invention can be used to quantify the activity of OPases such as those associated with paraoxonase or variants of paraoxonase including natural variants or artificially created mutant forms of paraoxonase.

In a further embodiment the compounds of the present invention can be used to quantify the activity of organophosphatases such as those associated with OPH or variants of OPH including natural variants or artificially created mutant forms of OPH.

In a further embodiment the presence of competing substrates (or compounds) for organophosphatase can be identified by inhibition of fluorescence in the presence of a substrate for OPH or paraoxonase. In a preferred embodiment, the substrate is DEPFMU and the competing substrate is an OP such as sarin or soman. In a further embodiment, paraoxonase is immobilized on a support and its activity is measured by the production of a fluorescent signal. Environmental extracts including water and air, extracts of swabs are added to paraoxonase and alternative substrates identified by a decrease in fluorescence. Environmental extracts may be extracted with aqueous or organic solvents, supercritical fluids, subcritical fluids, and the like.

In a further embodiment, OPH is immobilized on a support and its activity is measured by the production of a fluorescent signal. Environmental extracts including water and air, extracts of swabs are added to OPH and alternative substrates identified by a decrease in fluorescence. Environmental extracts may be extracted with aqueous or organic solvents, supercritical fluids, subcritical fluids, and the like.

A wide variety of organic and inorganic polymers, both natural and synthetic, may be employed as the material for immobilizing organophosphatases such as OPH or paraoxonase. Illustrative polymers include polyethylene, polypropylene, polymethacrylate, polyacrylate, rayon, nylon, cellulose, nitrocellulose, and polyvinylidene fluoride. The immobilized organophosphatase can be quantified by contacting with a compound of the present invention.

In a further embodiment, the present invention provides a method for monitoring decontamination of the environment of OPs. The extract of the soil treated with paraoxonase (for decontamination) can be contacted with a compound of the present invention, and the fluorescence produced can be an indication of the completeness of decontamination. In a still further embodiment, the compound of the present invention can be employed to identify soil-dwelling micro-organisms or plants which express either OPH and/or paraoxonase.

In a further embodiment the organophosphatase is coupled to a secondary structure such as an antibody with specificity for an alternative target such that the secondary structure binds to its target to form a organophosphatase-secondary structure: target complex. The organophosphatase may then be used as a reporter protein and the presence of the organophosphatase-secondary structure: target complex identified using the substrates or compounds of the present invention.

In a further embodiment, the PON1 gene is co-transfected with another protein of interest and used as a reporter gene for expression of the target protein. In a still further embodiment, the PON1 gene is under the control of different promoters and the fluorescent substrate used to determine the activity of different promoters.

In a further embodiment, the OPH gene is co-transfected with another protein of interest and used as a reporter gene for expression of the target protein. In a still further embodiment, the OPH gene is under the control of different promoters and the fluorescent substrate used to determine the activity of different promoters.

In a further embodiment the substrate is added to cells incubated with different molecules that may up-regulate the PON1 promoter and hence the expression of paraoxonase. Up-regulators of paraoxonase expression are identified by the increase in fluorescent signal in the presence of paraoxonase substrate. These regulators may affect signal transduction pathways that ultimately result in up-regulation of the gene promoter.

Unexpectedly, the replacement of two protons on the phosphate group of 6,8-difluoro-4-methylumbelliferyl phosphate by ethyl groups (and other low molecular weight groups, e.g., hydrocarbon groups) generates a poor substrate for serum or cell-derived phosphatases but a good substrate that is selectively hydrolyzed by serum and recombinant paraoxonases and OPH. This is in marked contrast to phosphatase specific substrates, such as 6,8-difluoro-4-methylumbelliferyl phosphate which is readily hydrolyzed by phosphatases, but not by paraoxonase. Thus, DEPFMU may be used as a paraoxonase specific substrate which can accurately detect serum paraoxonase activity even in the presence endogenous phosphatase. Consequently, a major advantage of DEPFMU over prior art, is the unexpectedly low specificity of this substrate to phosphatase and its high specificity for organophosphatases such as OPH and paraoxonase.

The present invention further provides a method for detecting and/or measuring the activity of organophosphatase including paraoxonase immobilized on a support comprising contacting the support with any of the compounds of formula I or II; measuring the fluorescence of a fluorescent product formed during the contacting; and correlating the measured fluorescence with the activity of the paraoxonase enzyme. In an embodiment, the support is a membrane, resin, biosensor, microtiter plate, nanotube or dipstick, fiber, silicon chip, magnetic beads, and different gels.

The present invention further provides a method for selectively detecting organophosphatase in a sample suspected to contain organophosphatase and a phosphatase comprising contacting the sample with any of the compounds of formula I or II, e.g., the compound of formula I, wherein $R^3$, $R^4$, $R^5$, $R^9$, and $R^{10}$ are selected from the group consisting of H and groups or atoms other than H, and $R^6$ and $R^8$ are halo or H; and the compound of formula II, wherein $X^4$-$X^9$ are O, m and n are 1, $R^{11}$-$R^{24}$ are H; measuring the fluorescence of a fluorescent product formed during the contacting; and correlating the measured fluorescence with the activity of the organophosphatase enzyme.

The present invention further provides a method for detecting and/or measuring the activity of organophosphatase enzyme immobilized on a support comprising contacting the support with any of the compounds of formula I or II; e.g., the compound of formula I, wherein $R^3$, $R^4$, $R^5$, $R^9$, and $R^{10}$ are selected from the group consisting of H and groups or atoms other than H, and $R^6$ and $R^8$ are halo or H; and the compound of formula II, wherein $X^4$-$X^9$ are O, m and n are 1, $R^{11}$-$R^{24}$ are H; measuring the fluorescence of a fluorescent product formed during the contacting; and correlating the measured fluorescence with the activity of the organophosphatase enzyme.

The substrates of the present invention provide unexpected specificity and sensitivity for detection of OPases even in the presence of the high acid and alkaline phosphatase activities found in cellular extracts, plasma and sera. The fact that the substrates of the present invention are even recognized by organophosphatases is surprising in view of the large size of the fluorogenic groups used relative to the known substrates for these proteins. Thus, there is no data available a priori to suggest that such a bulky substrate would be accessible to the active site of organophosphatases such as paraoxonase let alone selectively hydrolyzed by the protein.

The following examples further illustrate the invention but, of course, should not be construed as in any way limiting its scope.

EXAMPLE 1

This example demonstrates the specificity of 7-[diethyl-phospho]-,8-difluor-4-methylumbelliferyl towards paraoxonase.

The tested compounds included: 4-methylumbelliferyl acetate, 4-methylumbelliferyl oleate, 4-methylumbelliferyl heptanoate, 4-methylumbelliferyl palmitate, 6,8-difluoro-4-methylumbelliferyl-octanoate, 7-[diethyl-phospho]-6,8-difluoro-4-methylumbelliferyl [DEPFMU], and ELF-97 palmitate (Molecular Probes, OR), fluorescein diphosphate tetraethyl ester, (3-carboxypropyl)-trimethylammonium chloride 4-methylumbelliferyl ester, and 7-benzyloxy-6,8-difluoro-4-methylumbelliferyl. All compounds were evaluated for possible detection of paraoxonase activity using recombinant human paraoxonase, expressed in CHO cells. For expression of recombinant paraoxonase, human liver cDNA was obtained from Ambion Inc, (Austin, Tex.). Human PON1 cDNA was amplified by PCR with gene specific primers, TRSSP 216 [AAGAATTCCACCATGGC-GAAGCTGATTGCGCTC] [SEQ ID NO:1] and TRSSP 217 [AATCTAGATTAGAGCTCACAGTAAA-GAGCTTTGTG] [SEQ ID NO:2] containing Xba I and EcoRI restriction sites. Hassett C, Richter R J, Humbert R, Chapline C, Crabb J W, Omiecinski C J, Furlong C E. Characterization of cDNA clones encoding rabbit and human serum paraoxonase: the mature protein retains its signal sequence. *Biochemistry*, Oct 22;30(42):10141-9 (1991). Amplified PCR product containing PON1 cDNA was cloned into pBlueScript KS II vector (Stratagene, CA) as XbaI/ EcoRI fragment, sequenced from T3 and T7 primers to confirm identity of DNA and then subcloned into an expression vector containing EF-la promoter and GC-MSF poly (A) signal, forming expression vector pHLSS131. The expression vector DNA was propagated in E. coli, DH5a strain, and purified using Quagen Maxiprep kit for plasmid purification (Quagen, CA). CHO cells were obtained from ATCC and cultivated according to the recommended conditions. CHO cells were transfected with the expression vector using Fugene 6 reagent (Roche Diagnostic, Indianapolis, Ind.) according the manufacturer's manual. 48 hours after transfection, the level of PON1 expression was easily detectable by using standard substrates like paraoxon and phenylacetate. The test compounds were screened for paraoxonase mediated hydrolysis by incubation with transfected CHO cells. Fluorescent monitoring of the reaction was performed using SpectraMax GenimiXS fluorimeter, Molecular Devises Inc. (Sunnyvale, Calif.).

DEPFMU was specifically hydrolyzed by paraoxonase. After hydrolysis, highly fluorescent 6,8-difluoro-4-methylumbelliferyl is released. Since the DEPFMU itself does not possess any significant fluorescence, hydrolysis can be easily and safely monitored using any commercial fluorimeter with excitation at 355 nm and emmission at 460 nm.

EXAMPLE 2

This example illustrates an assay for detection of paraoxonase activity. DEPFMU may be used as a substrate for detection of serum derived as well as recombinant paraoxonase expressed in cell cultures. The following conditions have been used for the detection of paraoxonase in plasma. Samples of serum or plasma may be diluted 1 to 100 times in an assay buffer. This assay was performed in a 96 well "Nunc-immuno" plate. For example, 10 µl of diluted rabbit serum was added to each well of a 96 well plate containing 100 µl of assay buffer plus 100 µM of DEPFMU (stock DEPFMU was prepare as a 50 mM concentrate in dimethylformamide and stored at −20° C.). After thorough mixing the assay solution containing plasma was incubated for 20 min. at 37° C. Hydrolysis of DEPFMU was quantified by measuring the fluorescence level at 355/460 using a commercial fluorimeter. The level of fluorescence correlates with the level of 6,8-difluoro-4-methylumbelliferyl released from DEPFMU as result of paraoxonase mediated hydrolysis. The actual amount of 6,8-difluoro-4-methylumbelliferyl released in the assay may be calibrated with a known amount of 6,8-difluoro-4-methylumbelliferyl. An example of paraoxonase detection in different serum samples is presented in FIG. 1. Similar methods can be used for detection of recombinant paraoxonase expressed in cell culture.

Figure 2:
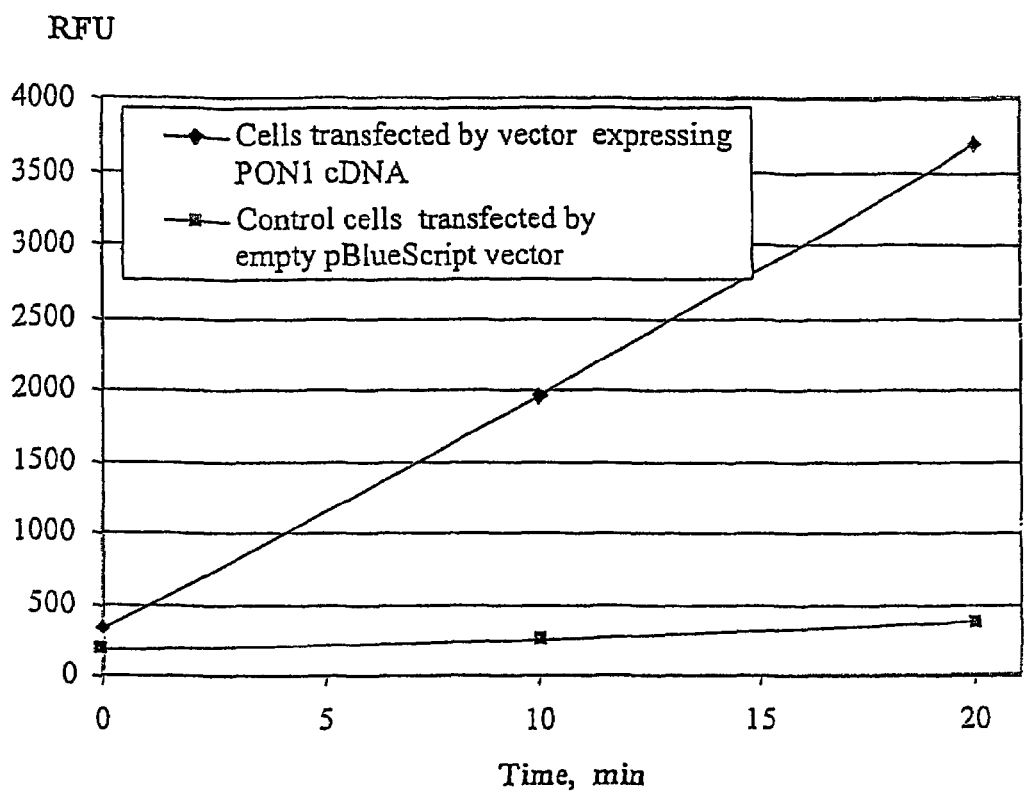
FIG. 2 depicts a cell membrane associated production of fluorescence in PON1 transfected and non-transfected CHO cells using DEPFMU as the substrate. In this experiment Chinese hamster ovary (CHO) cells were transfected using Fugene 6 reagent (Roche) with the expression vector pHLSS122 containing human PON1 cDNA. Transfection was performed in 96 well microtiter plates. 48 hours after transfection, the cells were washed twice with PBS and 100 µl of assay buffer containing 100 µm of DEPFMU were added. Immediately after addition, the rates of change of fluorescence at 37° C. were monitored at 355/460.

Since a significant percentage of recombinant paraoxonase stays associated with the cell membrane, methods were developed for evaluating the cell membrane associated paraoxonase. One such method harvests cells expressing paraoxonase, washes them twice with PBS (Dulbecco's Phosphate Buffer System) to remove endogenous paraoxonase which originates from either paraoxonase present in the growth medium or is synthesized and secreted by the cells. Washed cells are pelleted by centrifugation and resuspended in PBS at a density of up to $10^7$ cells/ml. 10 µl of the cell suspension is mixed with 100 µl of substrate solution per well of a 96 well microtiter plate, incubated for 20 min. and the fluorescence level measured as described above. As an option for this assay, adhesive cells may be plated into a microtiter plate a day or more before evaluation. The medium is then removed and the cells washed two times with PBS. 100 µl of substrate solution is added and fluorescence monitored after 20 or more minutes of incubation at 37° C. An example of the detection of membrane-associated paraoxonase is shown in FIG. 2. This shows the detection of paraoxonase activity with DEPFMU for CHO cells transfected with PON1 versus background fluorescence using non-transfected cells.

EXAMPLE 3

This example illustrates a method of detecting recombinant paraoxonase activity in CHO cells transfected with paraoxonase.

Human PON1 cDNA was recovered, cloned into pBlueScript KS II, and sequenced to confirm identity. For studies on the expression of paraoxonase PON1, cDNA was subcloned in expression vector under the control of the EF-1a promoter. CHO cells were transfected using Fugene 6 reagent with expression vector pHLSS122, containing human PON1 cDNA under EF-1a promoter in pBlueScript KS II cloning vector. Transfection with pBlueScript KS II vector DNA was performed for control CHO cells. Transfected cells were plated into 96 well tissue culture plates. 48 hours after transfection, the wells were washed twice with PBS and 100 µl of assay buffer containing 100 µM DEPFMU was added. Immediately after addition, the fluorescence of the wells was monitored using a 96 well SpectraMax Gemini XS fluorescence reader at 355/460.

Data from this experiment is presented on FIG. 2. Mock-transfected CHO cells do not hydrolyze DEPFMU, whereas cells transfected with the vector expressing paraoxonase catalyses significant hydrolysis of the substrate. Since the only difference between the two cell populations is that transfected cells express human paraoxonase activity whereas the control cells do not. This further demonstrates that the substrates of the present invention are highly specific for paraoxonase and there are no significant levels of enzyme in normal cells which are able to hydrolyze DEPFMU.

EXAMPLE 4

This example illustrates a method for measuring the Km of recombinant rabbit paraoxonase for DEPFMU.

Figure 3:
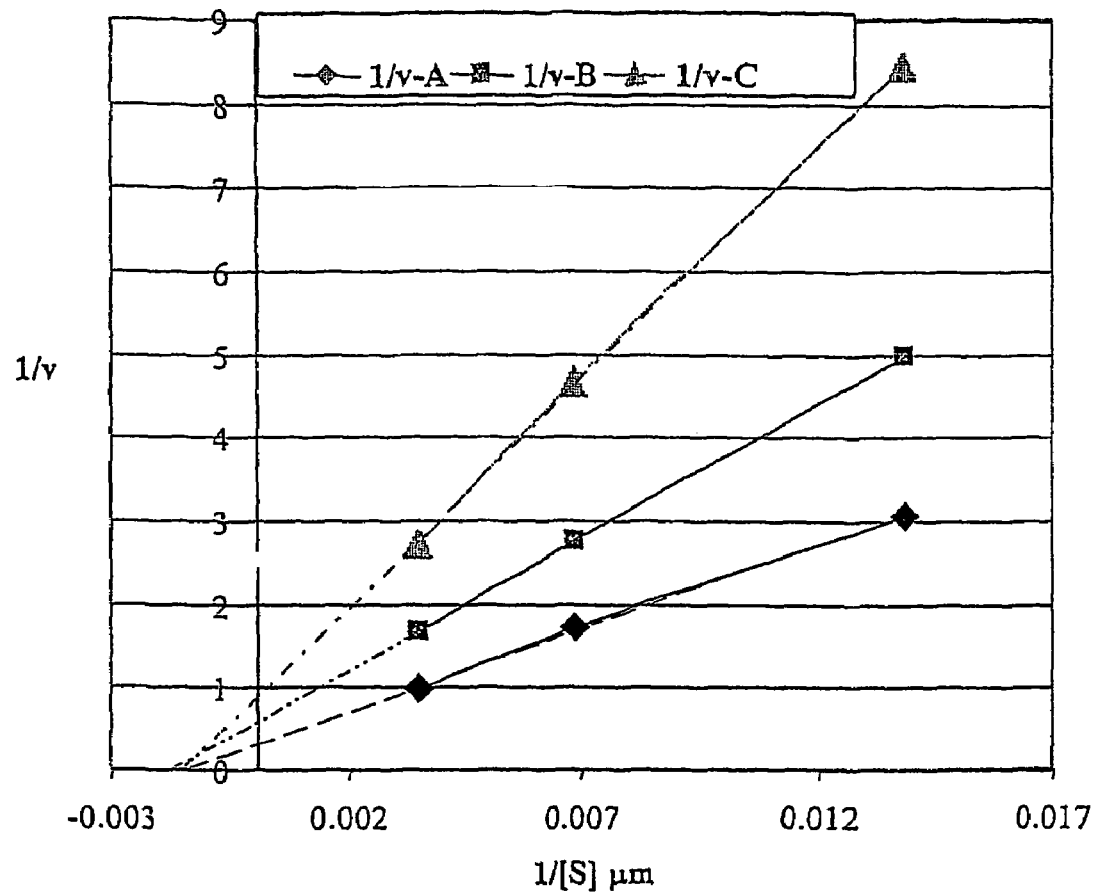
FIG. 3 depicts the measurement of the Km of DEPFMU for rabbit recombinant paraoxonase. The rabbit recombinant paraoxonase was expressed in CHO cells and partially purified. v-A, v-B and v-C are the velocities at ⅕, ⅒ and ¹⁄₂₀ dilutions of recombinant paraoxonase, respectively. Partially purified recombinant paraoxonase was mixed with solutions containing different concentrations of DEPFMU as substrate. The time-course of DEPFMU hydrolysis 37° C. was monitored using fluorescence reading at 355/460. The reciprocal of the Km of DEPFMU was obtained from the intercept on the abscissa using a Lineweaver-Burk Plot (1/v) where v is the velocity of the reaction against 1/[S] where [S] is the substrate concentration.

CHO cells were transfected with the plasmid pHLSS131 expressing rabbit PON1 cDNA. See example 1 and 2 for additional details of transfection and expression. After transfection the cells were propagated in growth medium, harvested and paraoxonase was partially purified from the cell membrane by extraction with 0.03% Tergitol (Sigma) in PBS. Extracted paraoxonase was separated from cells by centrifugation at 10000 g for 10 min. The supernatant was considered as partially purified paraoxonase. 10 µl of three different dilutions ⅕, ⅒ and 1/20 of recombinant paraoxonase (1/v-A, 1/v-B and 1/v-C) were incubated with 100 µl of serially diluted DEPFMU as the substrate at 37° C in a 96 well micro-titer plate. The time-course of DEFPMN hydrolysis was measured by monitoring fluorescence every 5 min at 355/460 as described above. Data on this experiment is presented in FIG. 3. Velocity of reaction was calculated as the change in the level of fluorescence over time. Stable velocity of reaction was observed up to 30 min of reaction. Actual Km of paraoxonase for DEPFMU was calculated as 666 µM. For comparison the Km of human paraoxonase for paraoxon is around 500 µM [9].

EXAMPLE 5

This example provides a comparison of the sensitivity of paraoxon and a compound of the present invention as a substrate for paraoxonase detection.

Figure 4:
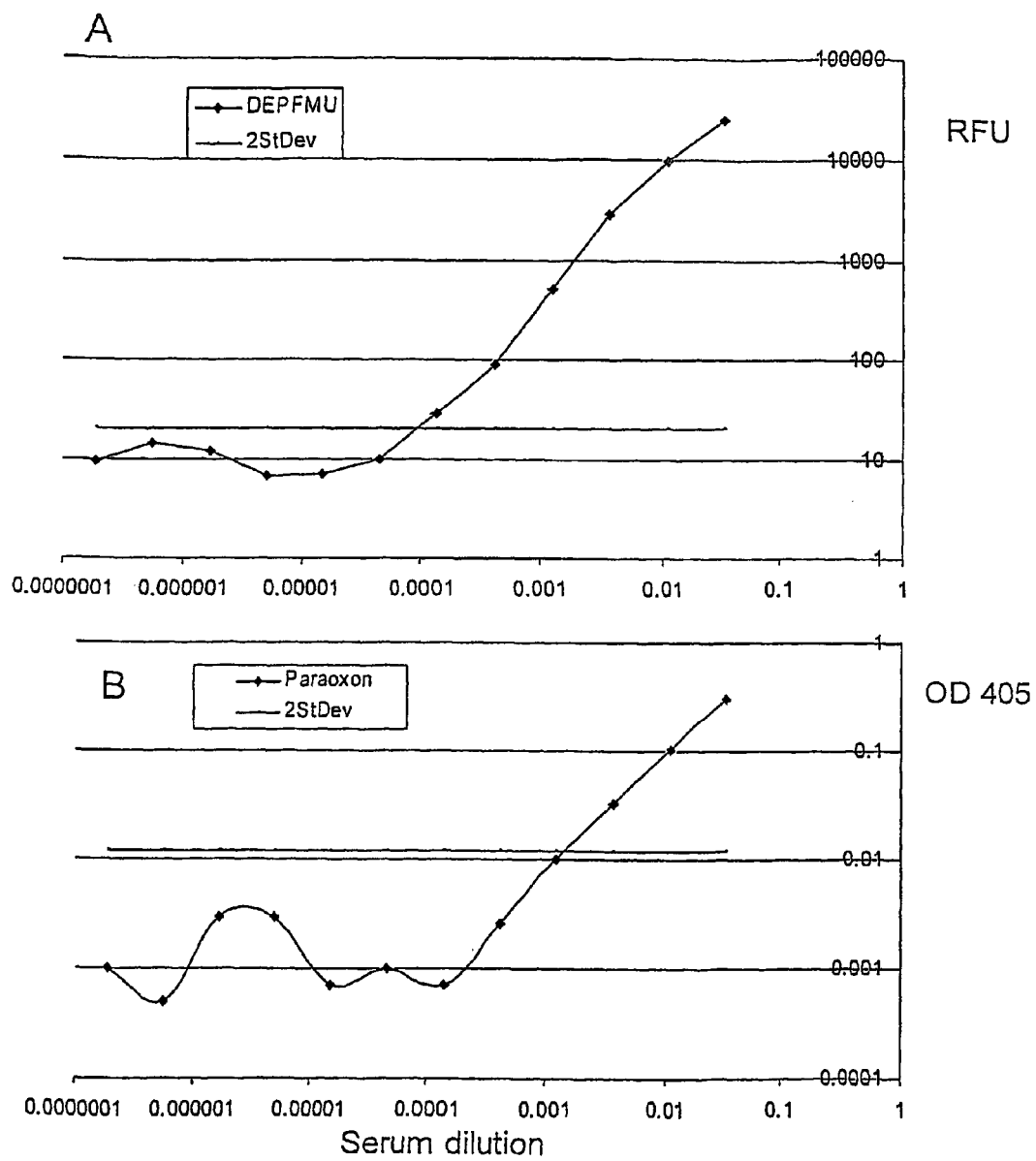
FIG. 4 depicts a comparison of the sensitivity of paraoxonase detection using paraoxon and DEPFMU based assays. An evaluation of the relative sensitivity of DEPFMU (A) and paraoxon (B) based assays for paraoxonase assay was performed using 10 µl serial dilution of rabbit serum samples incubated with 100 µl of assay buffer comprising 4 mM paraoxon or 100 µM DEPFMU in the assay buffer. After incubation, the optical density at 405 was measured to detect paraoxon and fluorescence (355/460) was read for DEPFMU. The two standard deviations above background readings is assigned as the limits of reliable detection. As can be seen from the figure, paraoxonase activity can be reliably detected with more that 1:10,000 dilution in the DEPFMU based assay, while less than 1:1,000 is required for detection with paraoxon based assay.

This experiment demonstrates the relative sensitivity of DEPFMU-based assay compared with paraoxon based assays. 10 µl of serially diluted samples of rabbit serum were incubated for 30 min at 37° C. in the presence of 100 µl of 4 mM paraoxon or 100 µl of 100 µM DEPFMU in the assay buffer described above. After incubation, the optical density change of paraoxon was measured at a wavelength of 405 nm and the fluorescence of DEPFMU hydrolysis was measured at 355/460. The data is presented in FIG. 4. Reliable detection of paraoxonase activity was considered to be greater than two standard deviation units above background. This experiment demonstrates that the limit of detection of enzyme activity for paraoxon-based assay was less than 1/1,000 dilution of serum whereas that for DEPFMU was greater than a 1/10,000 fold dilution. Thus, DEPFMU-based assays a significantly higher sensitivity. The sensitivity and velocity of fluorescent detection of DEPFMU was sub-optimal due to using a substrate concentration (100 µM), well below the Km of [~666 µM], whereas the assay using paraoxon was well above the Km.

EXAMPLE 6

This example illustrates the hydrolysis of DEPFMU and detection of PON1 activity in CHO cells transfected with different PON1 mutants.

Figure 5:
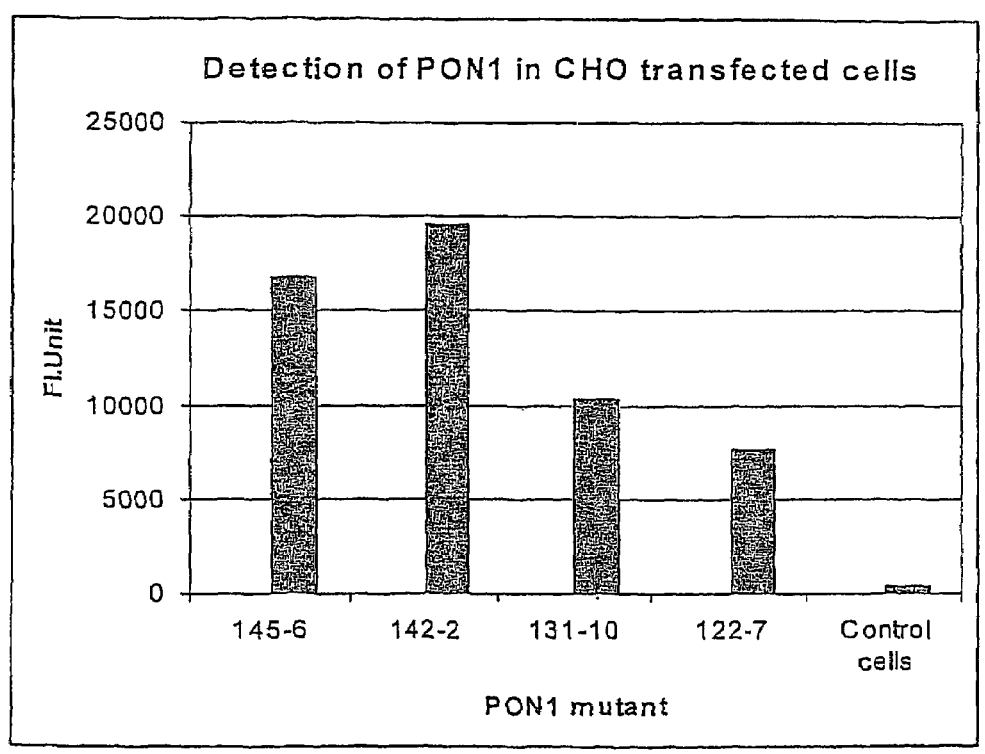
FIG. 5 depicts the hydrolysis of the DEPFMU by PON1 mutants.

$2\times10^5$ CHO cells in a 96 well plate were transfected by 1 µg of DNA with Fugene 6 reagent. DNA vector contained PON1 cDNA driven by EF-1 promoter. Since different natural variants of PON1 have different substrate specificity, four different variant/mutants of PON were used (145-6, 142-2, 131-10, and 122-7). 48 hours after transfection, cells were washed with PBS and 100 µl of the DEPFMU substrate were added. Final concentration of the substrate was 40 µg/mL in 50 mM Tris buffer pH 8.0, 100 mM NaCl, and 1 mM $CaCl_2$. After 10 min. of incubation at 37C, fluorescence was measured at 355 nm excitation and 460 nm emission. The results are shown in FIG. 5. All four mutants hydrolyzed the DEPFMU with very high efficiency. Spontaneous hydrolysis of substrate by CHO non-transfected cells was about 3%. The control CHO cell did not hydrolyze the substrate.

EXAMPLE 7

This example illustrates the sensitivity of detection provided by an embodiment of the present invention. We compared the sensitivity of detection of a serial dilution of OPH from 10 µg/ml to 0.5 µg/ml using different substrates including paraoxon and DEPFMU. 10 µl of OPH solution was mixed with 100 µl of buffer containing 100 µM of DEPFMU, or 1.2 mM of paraoxon. Samples were incubated for 30 min at 37° C. with changes in optical properties monitored every 5 min. Assuming a molecular weight of 39,000 kDa and 100% purity and activity of the protein as low as 1 femtomole (fmol) of OPH per well was reliably detected. For paraoxon the level of reliable detection was around 100 fmole of OPH per, well. The catalytic rate ($k_{cat}$) of OPH mediated hydrolysis was $1.5\times10^3$ $min^{-1}$ for DEPFMU and $4\times10^4$ $min^{-1}$ for paraoxon. Though the $k_{cat}$ for paraoxon was more than 10 times higher than the $k_{cat}$ for DEPFMU, the superior signal to noise ratio for the coumarin fluorophore over the optical change in nitrophenol, which was released after paraoxon hydrolysis, makes the DEPFMU based assay system approximately 100 times more sensitive for OPH detection than paraoxon. The Km of DEPFMU for OPH was analyzed. For this experiment 10 µl of OPH solution containing 25 fmoles of enzyme were mixed with 100 µl of 100 µM DEPFMU. The velocity of hydrolysis was constant only during the first 10 min of reaction and decreases after 10-15 min. A decline in hydrolysis was detected only after 25-30 min (data not shown) following OPH mediated hydrolysis of paraoxon. The Km of DEPFMU for OPH, was evaluated using concentrations of DEPFMU ranging from 290 µM to 2 µM. 10 µl of solution containing 25 fmoles of OPH were mixed with 100 µl of substrate solution. The reciprocal of the Km of DEPFMU was obtained from the intercept on the abscissa using a Lineweaver-Burk Plot (1/v) where v is the velocity of the reaction against 1/[S] where [S] is the substrate concentration. The apparent Km was calculated as 29 µM.

EXAMPLE 8

Figure 6A:
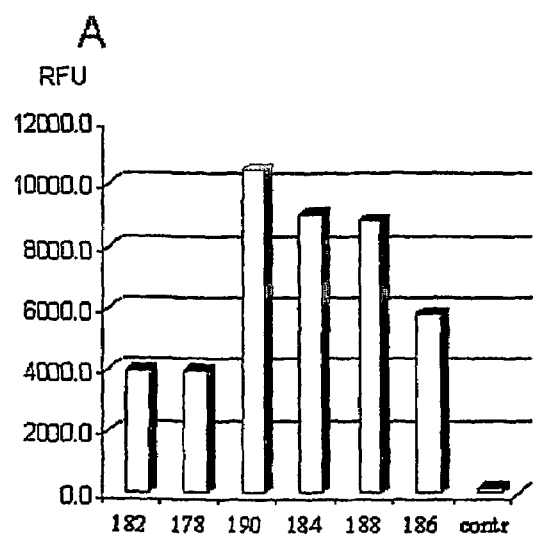
FIG. 6A depicts the hydrolysis data for a substrate of the present invention, DEPFMU.
Figure 6B:
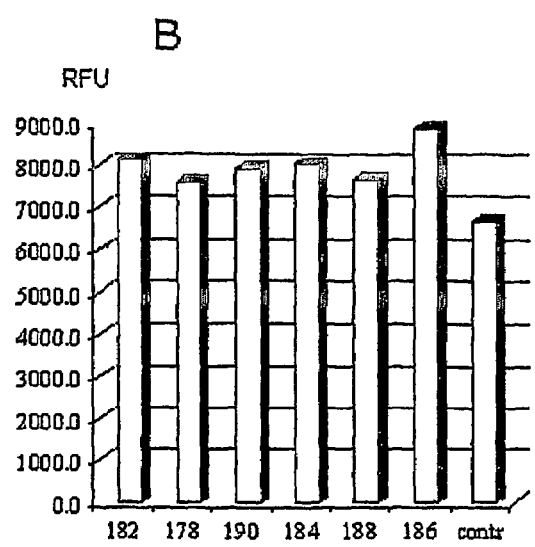
FIG. 6B depicts the hydrolysis data for 6,8-difluoro-4-methylumbelliferyl phosphate (DiFMUP). See Example 8.

This example illustrates a superior property of a substrate of the present invention, DEPFMU, relative to that of 6,8-difluoro-4-methylumbelliferyl phosphate (DiFMUP) as substrate for detection of paraoxonase. CHO cells were transfected using Fugene 6 reagent with the expression vector pHLSS122, containing human PON1 cDNA under EF-1a promoter in pBlueScript KS II cloning vector. Transfection with pBlueScript KS II vector DNA was performed for control CHO cells. Different plasmids 182, 178, 190, 184 188 and 186 containing different mutants and natural variants of PON1 were used for expression. Transfected cells were plated into 96 well tissue culture plates. 48 hours after transfection, the wells were washed twice with PBS and 100 µl of assay buffer containing 100 µM DEPFMU or 100 µM DiFMUP was added. Immediately after addition, the fluorescence of the wells was monitored using a 96 well SpectraMax Gemini XS fluorescence reader at an excitation wavelength of 355 nm and an emission wavelength of 460 nm. The data from this experiment is presented on FIGS. 6a and 6b. On FIG. 6a, DEPFMU hydrolysis by control and transfected cells was demonstrated. As it is seen from the figure, mock-transfected CHO cells do not hydrolyze DEPFMU, whereas cells transfected with the vector expressing paraoxonase catalyses significant hydrolysis of the substrate. FIG. 6b demonstrates data on DiFMUP hydrolysis by control and transfected CHO cells. The control cells as well as experimentally transfected cells do hydrolyze significant amount of DiFMUP, indicating there is significant PON1 independent hydrolysis of DiFMUP. Most probably this high level of hydrolysis is mediated by cell phosphatases, which are abundant in the majority of cell lines. The significant paraoxonase independent hydrolysis of DiFMUP precludes this substrate being useful for the detection of paraoxonase.

EXAMPLE 9

Figure 7:
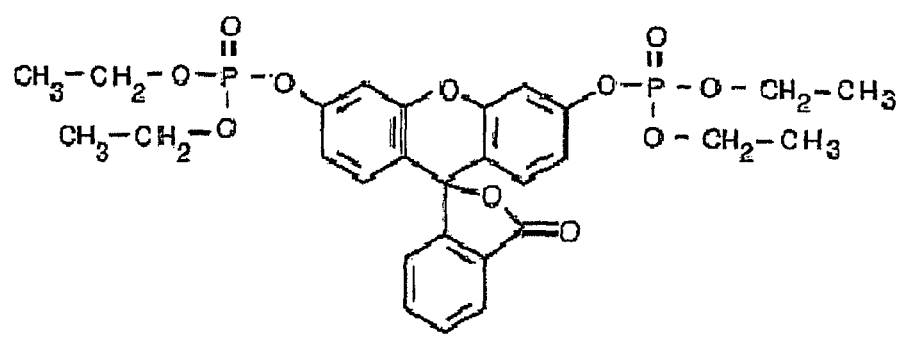
FIG. 7 depicts the hydrolysis of the fluorescein diphosphate tetra ethyl ester (FDPTEE) by bacterial OPH.
Figure 7:
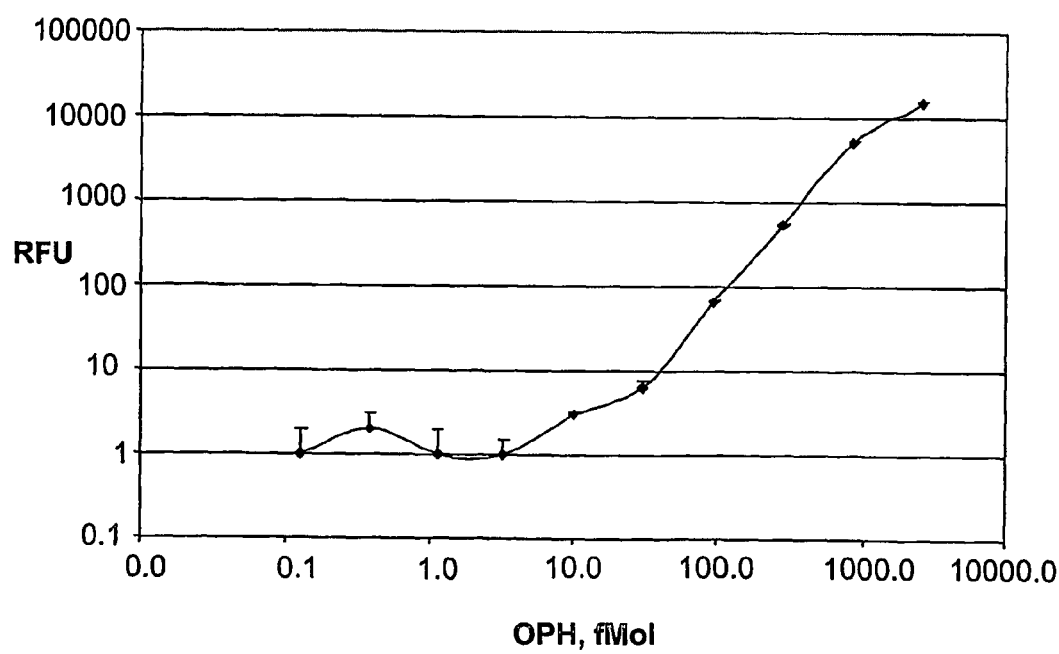

This example illustrates a method for the detection of organophosphatase. Fluorescein diphosphate tetraethyl ester (FDPTEE) was used as a substrate for detection of organophosphatase activity. The experiment was performed as described above in example 7. Briefly, serial dilution of OPH from 10 µg/ml to 0.5 ng/ml was prepared. 10 µl of the various dilution of OPH were mixed with 100 µl of buffer containing 100 µM of FDPTEE. Samples were incubated for 30 min at 37° C. and fluorescence (Ex 488 nm/Em 520 nm) was monitored every 5 min. The results obtained are shown in FIG. 7. Assuming that the enzyme has a molecular weight of 39,000 kDa and is 100% pure and fully active as low as 100 femtomole (fmol) of OPH per well was reliably detected, showing it to be applicable as a substrate for OPase.

Figure 8:
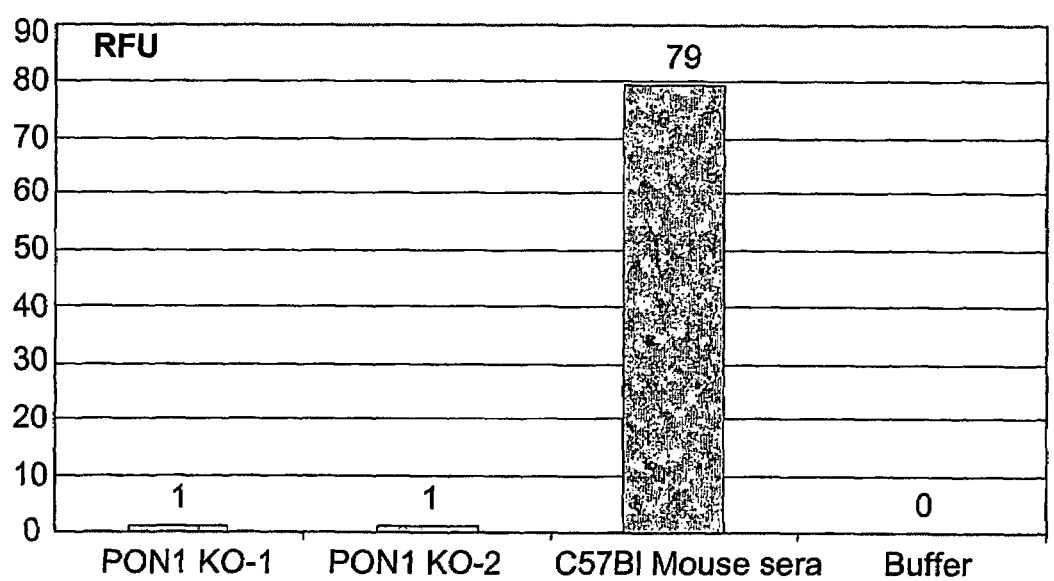
FIG. 8 depicts the hydrolysis of FDPTEE by normal mice contrasted with PON1 knock out mice.

The specificity of FDPTEE for paraoxonase was demonstrated using sera samples obtained from mice than had their PON1 gene destroyed through embryonic stem cell technology (PON1 KO) (10). In these experiments, 10 µl of sera samples from normal C57Bl/6 mice and PON1 KO C57 Black/6 mice were diluted 1/10 with 150 mM NaCl and 20 mM Tris pH 8.0. 10 µl of diluted sera were mixed with 100 µl of 100 µM FDPTEE and incubated for 30 min at 37° C. After incubation the level of fluorescence was measured (Ex 488 nm/Em 520 nm). The results obtained are shown in FIG. 8. No fluorescence was detected in samples of sera obtained from PON1 KO mice, whereas significant fluorescence was detected in sera samples obtained from normal C57Black mice. These data confirm that serum paraoxonase is the enzyme responsible for FDPTEE hydrolysis and generation of fluorescence signal in normal samples.

EXAMPLE 10

This example illustrates a method of preparing an embodiment of the compound of formula II, namely, fluorescein diphosphate tetraethyl ester. 2.5 g of fluorescein (7.5 mmol) is suspended in THF (60 mL) and anhydrous $CH_2Cl_2$ (mL). 3.1 g of 1H-tetrazole 3.1 g.(44 mmol) is added and stirred at room temperature for ~1.5 hours or until the reaction mixture becomes a transparent dark yellowish solution. The resulting solution is cooled to 0° C. and 5.0 g of diethyl N. N-diisopropylphosphoramidite (23 mmol) is added dropwise over a period of 3-4 minutes to yield a very light yellow solution. The cooling bath is removed and the reaction stirred at room temperature until TLC shows no starting material remains (~5 minutes). The reaction is cooled back to 0° C. $R_f$ (fluorescein diphosphite, tetraethyl ester)=0.7-0.75, a quenching spot that becomes fluorescent yellow upon heating; hexanes/EtOAc (3:2) A solution of 3-chloroperoxybenzoic acid (MCPBA) (5.5 g, 32 mmol) in $CH_2Cl_2/CHCl_3$ (9:1, 50 mL) is prepared, and washed with saturated NaCl (1×50 mL), followed by drying over $Na_2SO_4$. The dried solution is added to the 0° C. reaction mixture to yield a cloudy yellowish solution. The cooling bath is removed and the reaction stirred at room temperature until TLC indicates completion (~10 minutes). The solvent is removed from the reaction mixture in vacuo and the resulting yellow gum is dissolved in EtOAc (~100 mL). The solution is washed with 10-20% sodium thiosulfate/$H_2O$ (1×100 mL), saturated $NaHCO_3$ (1×100 mL), and saturated NaCl (1×100 mL), and dried over $Na_2SO_2$. The solvent is removed in vacuo. At this point, TLC in hexanes/EtOAc (3:2) shows two spots: $R_f$-0.65-0.7, a quenching spot that becomes fluorescent upon heating; and $R_f$-0.95-1.0, a quenching spot that does not fluoresce upon heating. 50 mL of methanol are added to the gum to precipitate the high-$R_f$ material. The solid is removed by filtration, and methanol is removed from the filtrate in vacuo. The resulting product is purified by column chromatography under the following conditions:

| Stationary Phase | medium $SiO_2$ |
|---|---|
| Mobile Phase | $CHCl_3$ → 50% $MeOH/CHCl_3$ |

About 50 mL of hexane is added to the resulting oily material to form a solid. The solid is collected with filtration and dried to constant weight in vacuo to yield FDP tetraethyl ester (fluorescein diphosphate tetraethyl ester) as a white sold. Actual yield 1.61 g (36%). $R_f(V)$=0.25, a quenching spot that becomes fluorescent yellow upon heating; EtOAc/hexanes (2:1)

REFERENCES

1. Aviram, M., Billecke, S., Sorenson, R., Bisgaier, C., Newton, R., Rosenblat, M., Erogul, J., Hsu, C., Dunlop, C., and La Du, B. (1998). *Paraoxonase active site required for protection against LDL oxidation involves its free sulfrydryl group and is different from that required for its arylesterase/paraoxonase activities: selective action of human paraoxonase allozymes Q and R*. Arterioscler Thromb Vasc Biol 18, 1617-24.
2. Mackness, B., Mackness, M. I., Arrol, S., Turkie, W., and Durrington, P. N. (1998). *Effect of the human serum paraoxonase 55 and 192 genetic polymorphisms on the protection by high density lipoprotein against low density lipoprotein oxidative modification*. FEBS Lett 423, 57-60.
3. Costa, L. G., Cole, T. B., Jarvik, G. P., and Furlong, C. E. (2003). *Functional genomic of the paraoxonase (PON1) polymorphisms: effects on pesticide sensitivity, cardiovascular disease, and drug metabolism*. Annu Rev Med 54, 371-92.
4. Johnson, K. J., Ward, P. A., Gorainick, S., and Osborn, M. J. (1977). *Isolation from human serum of an inactivator of bacterial lipopolysaccharide*. Am J. Pathol 88, 559-74.
5. La Du, B. N., Aviram, M., Billecke, S., Navab, M., Primo-Parmo, S., Sorenson, R. C., and Standiford, T. J. (1999). *On the physiological role(s) of the paraoxonases*. Chem Biol Interact 119-120, 379-88.
6. La Du, B., Draganov, D. I., Stetson, P. L., and Watson, C. E. (2000). *PON3 and uses thereof.* U.S. Pat. No. 6,573,370.
7. Costa, L. G., McDonald, B. E., Murphy, S. D., Omenn, G. S., Richter, R. J., Motulsky, A. G., and Furlong, C. E. (1990). *Serum paraoxonase and its influence on paraoxon and chlorpyrifos-oxon toxicity in rats*. Toxicol Appl Pharmacol 103, 66-76.
8. Li, W. F., Furlong, C. E., and Costa, L. G. (1995). *Paraoxonase protects against chlorpyrifos toxicity in mice*. Toxicol Lett 76, 219-26.
9. Josse, D., Xie, W., Renault, F., Rochu, D., Schopfer, L. M., Masson, P., and Lockridge, O. (1999). *Identification of residues essential for human paraoxonase (PON1) arylesterase/organophosphatase activities*. Biochemistry 38, 2816-25.
10. Shih D M, Gu L, Xia Y R, Navab M, Li W F, Hama S, Castellani L W, Furlong C E, Costa L G, Fogelman A M, Lusis A J. Mice lacking serum paraoxonase are susceptible to organophosphate toxicity and atherosclerosis. Nature. 1998 Jul. 16;394 (6690):284-7.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

imido, sulfo, sulfonyl, sulfinyl, sulfomethyl, salt of sulfomethyl, thiocyanato, aldehydo, keto, carbamoyl, urethane, ureido, guanidino, $C_1$-$C_6$ alkylamino, $C_1$-$C_6$ acylamino, $C_1$-$C_6$ alkylamido, $C_1$-$C_6$ alkyl, $C_1$-$C_6$ alkoxy, $C_1$-$C_6$ perfluoroalkyl, halomethyl, $C_1$-$C_6$ alkylthio, $C_5$-$C_8$ cycloalkyl, $C_1$-$C_6$ haloalkyl, $C_5$-$C_8$ halocycloalkyl, $C_1$-$C_6$ hydroxyalkyl, $C_5$-$C_8$ hydroxycycloalkyl, C 1-C6 alkoxy $C_1$-$C_6$ alkyl, $C_2$-$C_6$ alkoxycarbonyl, $C_2$-$C_6$ alkoxycarbonyl $C_1$-$C_6$ alkyl, carboxy $C_1$-$C_6$ alkyl, carboxy $C_1$-$C_6$ alkoxy, dicarboxy

---

---

What is claimed is:

1. A compound of the formula I:

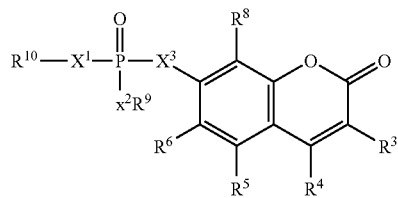

(I)

wherein
  $R^3$ is selected from the group consisting of H, cyano, $C_1$-$C_6$ alkyl, $C_1$-$C_6$ perfluoroalkyl, $C_2$-$C_6$ alkenyl, $C_2$-$C_6$ alkynyl, aryl, and heteroaryl, formyl, carboxamide of the formula —(C=O)NR$^1$R$^2$ where $R^1$ and $R^2$ are independently H, alkyl having 1-6 carbon atoms, an aryl, or $R^1$ and $R^2$ taken together form a saturated 5- or 6- membered ring having the formula —(CH$_2$)$_2$—M—(CH$_2$)$_2$— where the ring moiety M is a single bond, an oxygen atom, a methylene group, or the secondary amine —NR$^7$— where $R^7$ is H or alkyl having 1-6 carbon atoms;
  $R^4$ is selected from the group consisting of H, hydroxyl, cyano, nitro, halo, amino, amido, azido, acetal, ketal, $C_1$-$C_6$ alkyl, dicarboxy $C_1$-$C_6$ alkoxy, $C_2$-$C_6$ cyanoalkyl, phosphono $C_1$-$C_6$ alkyl, phosphoryl $C_1$-$C_6$ alkyl, mono-, di-, and trisaccharides, nucleic acids, oligonucleotides, amino acids, peptides, and proteins, and $C_2$-$C_6$ alkenyl, $C_2$-$C_6$ alkynyl, aryl, arylcarbonyl, and heteroaryl, which may be optionally substituted with a substituent selected from the group consisting of hydroxyl, cyano, nitro, halo, amino, amido, azido, acetal, ketal, imido, sulfo, sulfonyl, sulfinyl, thiocyanato, aldehydo, keto, carbamoyl, urethane, ureido, and guanidine;
  $R^5$ is H or $C_1$-$C_6$ alkoxy;
  $R^9$ and $R^{10}$ are ethyl;
  $R^6$ and $R^8$ are halo; and
  $X^1$, $X^2$, and $X^3$ are independently O or S.

2. The compound of claim 1, wherein $R^4$ is selected from the group consisting of H, cyano, sulfomethyl, salt of sulfomethyl, aryl, $C_1$-$C_6$ alkyl, $C_1$-$C_6$ alkoxy, and $C_1$-$C_6$ perfluoroalkyl.

3. The compound of claim 2, wherein $R^4$ is selected from the group consisting of $C_1$-$C_6$ alkyl.

4. The compound of claim 3, wherein $R^4$ is methyl.

5. The compound of claim 1, wherein $R^6$ and $R^8$ are fluoro.

6. The compound of claim 1, wherein $R^9$ and $R^{10}$ are ethyl, $R^4$ is methyl, and $R^6$ and $R^8$ are fluoro.

7. The compound of claim 1, wherein $X^1$, $X^2$, and $X^3$ are O.

8. The compound of claim 1, wherein $X^1$, $X^2$ and $X^3$ are S.

9. A method for specifically and selectively detecting and/or measuring the activity of an organophosphatase enzyme in a biological fluid, which contains at least oragnophosphatases and phosphatases, said method comprising:

(a) contacting the fluid with a compound of the formula I:

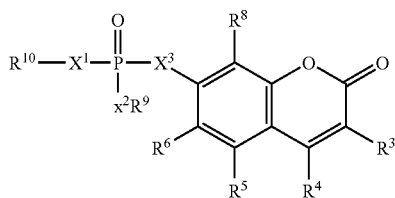

(I)

wherein $R^3$ is selected from the group consisting of H, cyano, $C_1$-$C_6$ alkyl, $C_1$-$C_6$ perfluoroalkyl, $C_2$-$C_6$ alkenyl, $C_2$-$C_6$ alkynyl, aryl, and heteroaryl, formyl, carboxamide of the formula —(C=O)$NR^1R^2$ where $R^1$ and $R^2$ are independently H, alkyl having 1-6 carbon atoms, an aryl, or $R^1$ and $R^2$ taken together form a saturated 5- or 6-membered ring having the formula —(CH$_2$)$_2$—M—(CH$_2$)$_2$— where the ring moiety M is a single bond, an oxygen atom, a methylene group, or the secondary amine —$NR^7$— where $R^7$ is H or alkyl having 1-6 carbon atoms;

$R^4$ is selected from the group consisting of H, hydroxyl, cyano, nitro, halo, amino, amido, azido, acetal, ketal, imido, sulfo, sulfonyl, sulfinyl, sulfomethyl, salt of sulfomethyl, thiocyanato, aldehydo, keto, carbamoyl, urethane, ureido, guanidino, $C_1$-$C_6$ alkylamino, $C_1$-$C_6$ acylamino, $C_1$-$C_6$ alkylamido, $C_1$-$C_6$ alkyl, $C_1$-$C_6$ alkoxy, $C_1$-$C_6$ perfluoroalkyl, halomethyl, $C_1$-$C_6$ alkylthio, $C_5$-$C_8$ cycloalkyl, $C_1$-$C_6$ haloalkyl, $C_5$-$C_8$ halocycloalkyl, $C_1$-$C_6$ hydroxyalkyl, $C_5$-$C_8$ hydroxycycloalkyl, $C_1$-$C_6$ alkoxy $C_1$-$C_6$ alkyl, $C_2$-$C_6$ alkoxycarbonyl, $C_2$-$C_6$ alkoxycarbonyl $C_1$-$C_6$ alkyl, carboxy $C_1$-$C_6$ alkyl, carboxy $C_1$-$C_6$ alkoxy, dicarboxy $C_1$-$C_6$ alkyl, dicarboxy $C_1$-$C_6$ alkoxy, $C_2$-$C_6$ cyanoalkyl, phosphono $C_1$-$C_6$ alkyl, phosphoryl $C_1$-$C_6$ alkyl, mono-, di-, and trisaccharides, nucleic acids, oligonucleotides, amino acids, peptides, and proteins, and $C_2$-$C_6$ alkenyl, $C_2$-$C_6$ alkynyl, aryl, arylcarbonyl, and heteroaryl, which may be optionally substituted with a substituent selected from the group consisting of hydroxyl, cyano, nitro, halo, amino, amido, azido, acetal, ketal, imido, sulfo, sulfonyl, sulfinyl, thiocyanato, aldehydo, keto, carbamoyl, urethane, ureido, and guanidine;

$R^5$ is H or $C_1$-$C_6$ alkoxy;

$R^9$ and $R^{10}$ are ethyl;

$R^6$ and $R^8$ are halo; and $X^1$, $X^2$, $X^3$ are independently O or S;

(b) measuring the fluorescence of a fluorescent product formed during the contacting; and (c) correlating the measured fluorescence with the activity of the organophosphatase enzyme.

10. The method of claim 9, wherein the organophosphatase is paraoxonase.

11. The method of claim 9, wherein the organophosphatase is OPH.

12. The method of claim 9, wherein $R^9$ and $R^{10}$ are ethyl, $R^4$ is methyl, $R^6$ and $R^8$ are fluoro, and $X^1$, $X^2$, and $X^3$ are O.

13. The method of claim 9, wherein K and $X^2$ are O, $X^3$ is S, $R^6$ and $R^8$ are H; $R^9$ and $R^{10}$ are ethyl, and $R^4$ is methyl.

14. The method of claim 9, wherein the fluid is a biological fluid.

15. The method of claim 14, wherein the biological fluid is selected from the group consisting of blood, blood-derived compositions, serum, cerebrospinal fluid, urine, saliva, milk, ductal fluid, tears, semen, cell or tissue extracts, culture medium from the expression of paraoxonase or mutations of paraoxonase, samples arising from the fractionation of paraoxonase or HDL from biological samples.

16. The method of claim 15, wherein the cell or tissue extract is of brain, artery, vein or gland.

17. The method of claim 14, wherein the fluid is an environmental fluid.

18. The method of claim 17, wherein the environmental fluid is an extract of soil, water, or swab.

19. A method for selectively detecting an organophosphatase in a sample suspected to contain an organophosphatase and a phosphatase comprising:

(a) contacting the sample with a compound of the formula I:

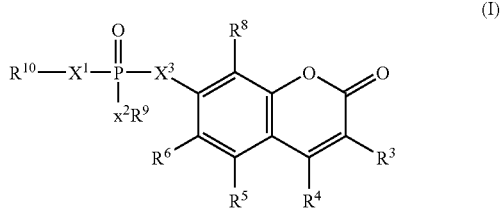

(I)

wherein $R^3$ is selected from the group consisting of H, cyano, $C_1$-$C_6$ alkyl, $C_1$-$C_6$ perfluoroalkyl, $C_2$-$C_6$ alkenyl, $C_2$-$C_6$ alkynyl, aryl, and heteroaryl, formyl, carboxamide of the formula —(C=O)$NR^1R^2$ where $R^1$ and $R^2$ are independently H, alkyl having 1-6 carbon atoms, an aryl, or $R^1$ and $R^2$ taken together form a saturated 5- or 6-membered ring having the formula —(CH$_2$)$_2$—M—(CH$_2$)$_2$— where the ring moiety M is a single bond, an oxygen atom, a methylene group, or the secondary amine —$NR^7$— where $R^7$ is H or alkyl having 1-6 carbon atoms;

$R^4$ is selected from the group consisting of H, hydroxyl, cyano, nitro, halo, amino, amido, azido, acetal, ketal, imido, sulfo, sulfonyl, sulfinyl, sulfomethyl, salt of sulfomethyl, thiocyanato, aldehydo, keto, carbamoyl, urethane, ureido, guanidino, $C_1$-$C_6$ alkylamino, $C_1$-$C_6$ acylamino, $C_1$-$C_6$ alkylamido, $C_1$-$C_6$ alkyl, $C_1$-$C_6$ alkoxy, $C_1$-$C_6$ perfluoroalkyl, halomethyl, $C_1$-$C_6$ alkylthio, $C_5$-$C_8$ cycloalkyl, $C_1$-$C_6$ haloalkyl, $C_5$-$C_8$ halocycloalkyl, $C_1$-$C_6$ hydroxyalkyl, $C_5$-$C_8$ hydroxycycloalkyl, $C_1$-$C_6$ alkoxy $C_1$-$C_6$ alkyl, $C_2$-$C_6$ alkoxycarbonyl, $C_2$-$C_6$ alkoxycarbonyl $C_1$-$C_6$ alkyl, carboxy $C_1$-$C_6$ alkyl, carboxy $C_1$-$C_6$ alkoxy, dicarboxy $C_1$-$C_6$ alkyl, dicarboxy $C_1$-$C_6$ alkoxy, $C_2$-$C_6$ cyanoalkyl, phosphono $C_1$-$C_6$ alkyl, phosphoryl $C_1$-$C_6$ alkyl, mono-, di-, and trisaccharides, nucleic acids, oligonucleotides, amino acids, peptides, and proteins, and $C_2$-$C_6$ alkenyl, $C_2$-$C_6$ alkynyl, aryl, arylcarbonyl, and heteroaryl, which may be optionally substituted with a substituent selected from the group consisting of hydroxyl, cyano, nitro, halo, amino, amido, azido, acetal, ketal, imido, sulfo, sulfonyl, sulfinyl, thiocyanato, aldehydo, keto, carbamoyl, urethane, ureido, and guanidine;

$R^5$ is H or $C_1$-$C_6$ alkoxy;

$R^9$ and $R^{10}$ are ethyl;

$R^6$ and $R^8$ are halo; and $X^1$, $X^2$, $X^3$ are independently O or S;

(b) measuring the fluorescence of a fluorescent product formed during the contacting; and (c) correlating the measured fluorescence with the activity of the organophosphatase enzyme.

20. The method of claim 19, wherein the organophosphatase is paraoxonase.

21. The method of claim 19, wherein the organophosphatase is OPH.

22. The method of claim 19, wherein $R^9$ and $R^{10}$ are ethyl, $R^4$ is methyl, $R^6$ and $R^8$ are fluoro, and $X^1$, $X^2$, and $X^3$ are O.

23. The method of claim 19, wherein $X^1$ and $X^2$ are O, $X^3$ is S, $R^6$ and $R^8$ are H; $R^9$ and $R^{10}$ are ethyl, and $R^4$ is methyl.

24. A method for specifically and selectively detecting and/or measuring the activity of an organophosphatase enzyme immobilized on a support, which comprises at least organophosphatases and phosphatases, said method comprising:

(a) contacting the support with a compound of the formula I:

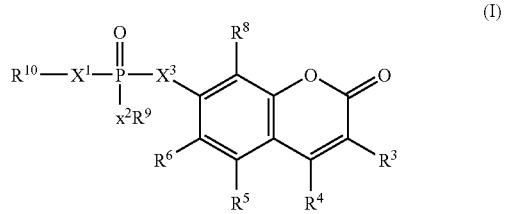

(I)

wherein $R^3$ is selected from the group consisting of H, cyano, $C_1$-$C_6$ alkyl, $C_1$-$C_6$ perfluoroalkyl, $C_2$-$C_6$ alkenyl, $C_2$-$C_6$ alkynyl, aryl, and heteroaryl, formyl, carboxamide of the formula —(C═O)NR$^1$R$^2$ where $R^1$ and $R^2$ are independently H, alkyl having 1-6 carbon atoms, an aryl, or $R^1$ and $R^2$ taken together form a saturated 5- or 6-membered ring having the formula —(CH$_2$)$_2$—M— (CH$_2$)$_2$— where the ring moiety M is a single bond, an oxygen atom, a methylene group, or the secondary amine —NR$^7$— where $R^7$ is H or alkyl having 1-6 carbon atoms;

$R^4$ is selected from the group consisting of H, hydroxyl, cyano, nitro, halo, amino, amido, azido, acetal, ketal, imido, sulfo, sulfonyl, sulfinyl, sulfomethyl, salt of sulfomethyl, thiocyanato, aldehydo, keto, carbamoyl, urethane, ureido, guanidino, C 1-C6 alkylamino, $C_1$-$C_6$ acylamino, $C_1$-$C_6$ alkylamido, $C_1$-$C_6$ alkyl, $C_1$-$C_6$ alkoxy, $C_1$-$C_6$ perfluoroalkyl, halomethyl, $C_1$-$C_6$ alkylthio, $C_5$-$C_8$ cycloalkyl, $C_1$-$C_6$ haloalkyl, $C_5$-$C_8$ halocycloalkyl, $C_1$-$C_6$ hydroxyalkyl, $C_5$-$C_8$ hydroxycycloalkyl, $C_1$-$C_6$ alkoxy $C_1$-$C_6$ alkyl, $C_2$-$C_6$ alkoxycarbonyl, $C_2$-$C_6$ alkoxycarbonyl $C_1$-$C_6$ alkyl, carboxy $C_1$-$C_6$ alkyl, carboxy $C_1$-$C_6$ alkoxy, dicarboxy $C_1$-$C_6$ alkyl, dicarboxy $C_1$-$C_6$ alkoxy, $C_2$-$C_6$ cyanoalkyl, phosphono $C_1$-$C_6$ alkyl, phosphoryl $C_1$-$C_6$ alkyl, mono-, di-, and trisaccharides, nucleic acids, oligonucleotides, amino acids, peptides, and proteins, and $C_2$-$C_6$ alkenyl, $C_2$-$C_6$ alkynyl, aryl, arylcarbonyl, and heteroaryl, which may be optionally substituted with a substituent selected from the group consisting of hydroxyl, cyano, nitro, halo, amino, amido, azido, acetal, ketal, imido, sulfo, sulfonyl, sulfinyl, thiocyanato, aldehydo, keto, carbamoyl, urethane, ureido, and guanidine;

$R^5$ is H or $C_1$-$C_6$ alkoxy;

$R^9$ and $R^{10}$ are ethyl;

$R^6$ and $R^8$ are halo; and $X^1$, $X^2$, and $X^3$ are independently O or S;

(b) measuring the fluorescence of a fluorescent product formed during the contacting; and (c) correlating the measured fluorescence with the activity of the organophosphatase enzyme.

25. The method of claim 24, wherein the organophosphatase is paraoxonase.

26. The method of claim 24, wherein the organophosphatase is OPH.

27. The method of claim 24, wherein the support is a membrane, resin, biosensor, microtiter plate, nanotube or dipstick.

28. The method of claim 24, wherein $R^9$ and $R^{10}$ are ethyl, $R^4$ is methyl, $R^6$ and $R^8$ are fluoro, and $X^1$, $X^2$, and $X^3$ are O.

29. The method of claim 24, wherein $X^1$ and $X^2$ are O, $X^3$ is S, $R^6$ and $R^8$ are H; $R^9$ and $R^{10}$ are ethyl, and $R^4$ is methyl.

* * * * *

SEQUENCE LISTING

<160> NUMBER OF SEQ ID NOS: 2

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 1
aagaattcca ccatggcgaa gctgattgcg ctc                             33

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 2
aatctagatt agagctcaca gtaaagagct tgtg                            35